United States Patent [19]
Van Der Laan et al.

[11] Patent Number: 5,891,703
[45] Date of Patent: Apr. 6, 1999

[54] MUTATED PENICILLIN G ACYLASE GENES

[75] Inventors: Jan M. Van Der Laan, Breda; Adriana M. Riemens, Delft; Wilhelmus J. Quax, Voorschoten, all of Netherlands

[73] Assignee: Gist-Hrocades, Delft, Netherlands

[21] Appl. No.: 793,229

[22] PCT Filed: Aug. 14, 1995

[86] PCT No.: PCT/EP95/03249

§ 371 Date: Apr. 23, 1997

§ 102(e) Date: Apr. 23, 1997

[87] PCT Pub. No.: WO96/05318

PCT Pub. Date: Feb. 22, 1996

[30] Foreign Application Priority Data

Aug. 12, 1994 [EP] European Pat. Off. .............. 94202314

[51] Int. Cl.⁶ .............................. C12N 9/84; C12N 15/11; C12N 15/55; C12N 15/70
[52] U.S. Cl. .............................. 435/230; 435/44; 435/45; 435/69.1; 435/172.3; 435/252.3; 435/252.33; 435/320.1; 536/23.2; 935/10; 935/14; 935/29; 935/73
[58] Field of Search ................................ 435/69.1, 172.3, 435/252.3, 252.33, 252.34, 320.1, 230, 44, 45; 536/23.2

[56] References Cited

U.S. PATENT DOCUMENTS

| | | | |
|---|---|---|---|
| 4,774,179 | 9/1988 | Ichikawa et al. | 435/51 |
| 5,168,048 | 12/1992 | Quax | 435/69.1 |
| 5,192,678 | 3/1993 | Iwami et al. | 435/228 |
| 5,320,948 | 6/1994 | Iwami et al. | 435/47 |
| 5,457,032 | 10/1995 | Quax et al. | 435/43 |
| 5,695,978 | 12/1997 | Quax | 435/230 |

FOREIGN PATENT DOCUMENTS

| | | |
|---|---|---|
| 0283218 | 9/1988 | European Pat. Off. . |
| 0322032 | 6/1989 | European Pat. Off. . |
| 0 453 048 | 10/1991 | European Pat. Off. . |
| 0558241A2 | 9/1993 | European Pat. Off. . |
| WO 95/12680 | 5/1995 | WIPO . |

OTHER PUBLICATIONS

Martin et al., *Biochim. Biophys. Acta*, 1037 (2), 133–139 (1990).
Prieto et al., *Appl. Microbiol. Biotechnol.*, 33 (5), 553–559 (1990).
Williams et al., *J. Cell. Biochem.*, 9(b) (Suppl.), 99 (1985).
Barbero et al., *Gene*, (1986) 49: 69–80.
Daumy, *J. Bacteriol*, (1985) 163:1279–1281.
Forney et al., *Applied & Environmental Microbiology*, (1989) 55: 2550–2555.
Forney et al., *Applied & Environmental Microbiology*, (1989) 55: 2556–2560.
Joris et al., *Biochem. J.*, 250, 313–324 (1988).
Matsuda et al., *J. Bacteriol*, (1987) 169: 5815–5820.
Matsuda et al., *J. Bacteriol*, (1987) 169: 5821–5826.
Norrander et al., *Gene*, (1983) 26: 101–106.
Schumacher et al., *Nucleic Acids Research*, (1986) 14: 5713–5727.
Stanssens et al., *Nucleic Acids Research*, (1989) 12: 4441–4454.

*Primary Examiner*—Dian C. Jacobson
*Assistant Examiner*—William W. Moore
*Attorney, Agent, or Firm*—McDonnell Boehnen Hulbert & Berghoff

[57] ABSTRACT

New mutant β-lactam Penicillin G acylases are provided, exhibiting altered substrate specificities. These Penicillin G acylases are obtained by expression of a gene encoding for said Penicillin G acylase and having an amino acid sequence which differs at least in one amino acid from the wild-type Penicillin G acylase.

12 Claims, 13 Drawing Sheets

```
afae_A    0
ecol_A    0
kcit_A    0
avis_A    0                                                                              18
pret_A    1  MKKHLISIAIVLSLSSLSLSSFS*STQIKIE***N****   QVQSVEVMRDSYGVPHVFADSHYGLYY
                                                  21                                     20
                                                 AKNEG*KVNF*****LY*KNKKD***E
                                                  31                                     20
                                                 ASPPTE*KIV****E***M****IY**DT*R*F*
                                                   9                                     19
                                                              ****M****IY*NDT*S*F*
                                                  10                                     41
                                                 EQSSEIKIV***E*****************IY**NDT*S*F*
                                                  11                                     18
                                                                                  NDTWH*F* afae_A   28                                      48                                     68
         GYGYAVAQDRLFQMDMARRSFVGTTAAVLGPGEQDAYVVKYDMQVRQ    NFT
ecol_A   30 ****V***********E*************TQ**V*E***         KDF**F*KDI*R*      *YW
                                                 50                              66
kcit_A   30 ****V***********E*************TQ*********       K*F*SF*KDI***      *YW
                                                 50                              66
avis_A   29 ***VM*K*********************LE*FGNEVSEIF*    ED*LSK*E*S*RDGYS
         51                                      49                              65
pret_A   *  ********************E********TQ**VSE*F*        KD*ISF*KEI**N      *YW
                                                 71                              87
                                                 80 afae_A   77                                      97                             116
         PASIQRQIAALSKDERDIFRGYADGYNAYLEQVRRRPE             LLPKEYVDFDF
ecol_A   75 *DA*RA*********PEDMS*LQ***M*WIDK*NTNT*       QFNT*G*
         85                                      95                             115
kcit_A   75 *D***RA****S**AEDKS*LQ*****M***WIDK*NAS*DK***        QQFST*G*
         85                                      95                             115
avis_A   75 NE*KKM*DG*DRQP*ELIAKF*E*ISR*VNEALKD*DDK*S**          FHEYQ*
         96                                     116                             115
pret_A   *  D*HKNQ*PSQ*QL******MWIK***INTK*DD*M*QFIY*
                                                106                             136
```

Fig. 2a

```
afae_A   126 QPEPLTDFDVVMIWVGSMANRFSDTNLEVTALAMRQSLEKQHGPERGRAL 166
ecol_A   125 TKRWEPAF*****STS*IDN***LLTA*KDKY*VSQ*M*V 165
kcit_A   125 KKHWEPAF*****STS*IDN***LLTA*KDKY*NDE*M*V 165
avis_A   146 L**QKW*ST*RVYMVTYLWIIRLKNAEILAKHEY*T*VS*KM 186
pret_A   146 L**SQW*S**A*M**T*****M*S*IDN***LLTA*KDKY*EQL*VEF 186 afae_A   176 FDELLWINDTTAPTTVPAPAAEHKPQA                         0
ecol_A   175 *NQ*KLVNPS**IAVQESNYPLKFNQQNSQTA                205
kcit_A   175 *NQ*KLVNPS**IA*RESSYPLKFDLQNTQTA                205
avis_A   174 *D*VPS*****SIVSEGKPKRESSSQSLQKL                 204
pret_A   196 *NQIN*L*NPN*****ISSEEFTYSDSQKTKNISQLNQISDYRLTAPMFER 236 pret_A   246 TAKDTTGKVLALSSQENNALIAKQYEQSGANGLAGYPTT             0
```

Fig. 2b

```
afae_B    1 SNLWSTRPERVQEGSTVLINGPQFGWYNPAYTYGIGLHGAGFDVVGNTPF
ecol_B    1 * * M * VIGKSKA * * * * * * * * * * * * * * * * * * * * * A * * * * * * * * * Y * * T * * * * *
kcit_B    1 * * M * VIGKNKA * DAKAIMV * * * * * * * * * * * * * * A * * * * * * * * * Y * * T * * * * *
avis_B    1 * * AAIVGS * KSAT * NAL * FS * * * * * * V * FVA * GFL * EV * * AP * * * ME * SGFI
pret_B    1 * * V * LVGKTKASGAKAI * L * * * * * * * * * * * F * * * * * * * * * * * * * NI * * * * afae_B   51 AYPIVLFGTNSEIAWGATAGPQDVVDIYQEKLNPSRADQYWFNNAWRTME
ecol_B   51 * * * * * GLG * * H * GV * S * * * * FG * D * * * * FA * R * SAEKPGY * LH * GK * VK * L
kcit_B   51 * * * * * GLV * * H * GT * S * * * * FG * D * * * * FA * * SAEKPGY * QH * GE * VK * L
avis_B   51 G * FIM * A * NHF * LS * * * * * * * YGN * T * * * * FE * * * * TKNSS * LYKGK * * D * *
pret_B   51 * * AI * * H * GHVS * * * * * * * FG * G * * * * FA * QVS * EDPNS * LHQGQ * KK * L afae_B  101 QRKERIQVRGQADREMTIW    119 RTVHGPVMQFDYDQGAAYSKKRSWDGY
ecol_B  101 S * E * T * T * KNGQAETF * V * 119 * * * * NIL * T * QTTQT * * A * S * A * * K
kcit_B  101 S * * * T * A * KDGQPET̂F * V * 119 * * LD * N * IKT * TRTQT * * A * A * A * A * * K
avis_B  101 K * * SFT * K * DNGEKK * VEKIYY  121 * * ISR * ETNKV * * YV * FR * T
pret_B  101 S * Q * TLN * K * EQPITFE * Y  119 N * VKR * KTTHT * * * A * A * * * K
```

Fig. 2c

```
afae_B   146 EVQSLLAWLNVAKARNWTEFLDQASKMAIS 176 INWYYADKHGNIGYVSPAF
ecol_B   146 * * * A * * * * * * * THQM * * * K * * Q * WTQ * * A * Q * 176 * * * * * * * * * * * * * HTGA
kcit_B   146 * * * AA * * * * * * THQM * * * K * * P * WTQ * * A * Q * 176 * * * * * * * * * * * * * HTGA
avis_B   151 E * * A * * MS * YMKANW * LK * * ENA * * EYTM * L 181 * * * * K * D * A * YHVGR
pret_B   146 * LT * * * M * * * VKQGQ * Q * * QQW * * * * * * QNQ * LT 176 * * * * * * * * * * * * * HTGH afae_B   196 LPQRPADQDIRVPAKGDGSMEWLGIKSFDAIPKAYNPPQGYLVNWNNKPA 236
ecol_B   196 Y * D * QSGH * P * L * * VP * T * KWD * K * LLP * EMN 226 * * * * * * * * * * * * QS * * IA * * * * * * * * * *
kcit_B   196 Y * D * QPGH * P * L * * VP * * * KWD * * * * LL * 225 * * V * * * * * * * QS * * IA * * * * * * * * * *
avis_B   201 Y * V * NNKI * E * * I * TP * T * EY * * K * FIP * KEN 231 * HVI * * KN * V * * * * * * * * S
pret_B   196 Y * D * QINH * P * L * * VS * T * EWD * K * * QP * ANN 226 * * V * * * * KS * * IA * * * * * * * * * * afae_B   246 PDKTNTDTYYWTYG   DRMNELVSQYQQKDLFSVQEIWEFNQKASYSDVN 284
ecol_B   246 K * YPAS * LFAFLW * GA * * VT * IDRLLE * * PRLTADQA * 276 DVIRQT * RQ * L * LL
kcit_B   245 K * YPAS * LFAFLW * GA * * VT * IDTILDKQPR * TADQA * 275 DVIRQT * LR * LL
avis_B   251 KEWV * GEYS * YWGEDNRVQQYINGGMEARGKVTLED * N * I * YT 281 * * FAQLR
pret_B   246 KNYPAS * LFAFLW * SA * * VK * IDNRIEAY * KLTADDM * AIL 276 * QT * RV * L *
```

Fig. 2d

```
              294                        304                        314  316         324                332
afae_B        WRYFRPHLEKLAQQLPADDSSKAALTMLLAWDGMEQDQ  GGQNAGPARV
              296                        306            316         326  336
ecol_B        L * L * T * QAATSG * TQS * PRRQLVET * TR * * INLLNDD * KTWQQ * GSA
              294                        304            314         324  334
kcit_B        * L * A * KDATAN * AEN * PRRQLVDK * AS * * ENLVNDD * KTYQQ * GSA
              301                        311            321         331  341
avis_B        ANL * K * L * IDVLDKNKSTNGNYTY * IEK * EEWNNLKEDENKDGYYDAGIA
              296                        306            316         326  336
pret_B        H * L * T * F * TQAT * G * * SN * N * VKLVS * * QQ * * IN * LSSD * KHYIH * GSA 342                        352                        362  366         372                382
afae_B        LFKTWLEEMYKQVLMPVVPESHRAMYSQTGFATQQGPNPGSINLSMGTKV
              346                        356            366         376
ecol_B        ILNV * * TS * L * RTVVAA * * MPFDKW * * AS * YE * T * DGPT * * LI * V * A * I
              344                        354            364         374
kcit_B        ILNA * * TS * L * RT * VAA * * APFGKW * * AS * YE * T * DGPT * * LI * V * A * I
              351                        361            371         381  391
avis_B        A * FDEWWNNLHDK * FMDELGDFYGITKEITDHRYGASLAYKNISKES * NY
              346                        356            366         376  386
pret_B        YLDI * * K * * L * AT * GQT * * APFDKW * LAS * YE * T * EGPT * * LI * T * A * L 392                        402                        412  416         422                432
afae_B        LLRALVLEAHPDDPKRVNVFGERSSQEIMHTALQNAQARLSQEQGAQMARW
              396                        406            416         426  436
ecol_B        * YE * VQGDKS * I * QA * DL * AGKPQ * * VVLA * * EDTWET * * KRY * NNVSN *
              394                        404            414         424  434
kcit_B        * YE * * QGDKS * I * QA * DL * * GKPE * * VILA * * DD * WQT * * KRY * NDVTG *
              401                        411            415         425  435
avis_B        KWVKW * NVDQE      KIIME * TN * VLAKLQSEKGLKAEKWRMPI
              396                        406            416         426  436
pret_B        * YES * LEDKS * ISQSIDL * SGPQNDVIRKT * NTTYQKMIEKY * DNP * N *
```

Fig. 2e

```
afae_B  442 TMPTSVHRFSDKNFTGTPQTMPGNTFAFTGYQNRGTENNRVVFDAKG
ecol_B  446 KT*AMALT*RAN****F*V**AAAEE*RHQAE********DMI**SPTTSDR 486
kcit_B  444 KT*AMALT*RAN****F*VAAAKEARHQAE****DMISPTSGNR 484
avis_B  440      KTMTFGEKSLIGIPHGY GSMTPIIEM****S***HYIEMTP**  475
pret_B  446 QT*ATALT*REN**FI**AL*QEN*HQNE*H***DLIT     486 afae_B  488 VEFCDAMPPGQSGFTDRNGVRSPHYEDQLKLYENFECKTMDVTHADIRR 536
ecol_B  496 P*LAW*VVA*******IAPD*TVDK************M*GR*SLWL*KQ*VEA 534
kcit_B  494 P*LAW*VVA*******IAPD*KADKD*******M*GR*SLWL*PQ*VDE 521
avis_B  481 PSGFNIT******I**VKKD*TI*D****************VMFAEWKF*PYLFNKK* 532
pret_B  492 G*SAW*VVA*******ISPQ*KP*Q*QS*QQ*GK*PLWLNSE*VAP afae_B  538 NAQSSTMLLIQPQP    o    o    o    o
ecol_B  546 HKE*QEV*HV*R      o    o    o    o
kcit_B  544 HKE*QEV*Q V*R     o    o    o    o
pret_B  542 YIE*TET*I*ER
```

Fig. 2f

MUTATED PENICILLIN G ACYLASE GENES

FIELD OF THE INVENTION

The present invention relates to mutations of prokaryotic Penicillin G acylase or its preenzyme or preproenzyme, resulting in altered properties of the mutant penicillin G acylase.

BACKGROUND OF THE INVENTION

The basic antibiotics of the β-lactam type are principally obtained by fermentation. Fungi of the genus Penicillium and Cephalosporium (Acremonium) are used for the production of raw material for β-lactam antibiotics as penicillin G, penicillin V and cephalosporin C. These fermentation products, also referred to as PenG, PenV and CefC, respectively, are the starting materials for nearly all currently marketed penicillins and cephalosporins. In general the acyl group at the 6-amino of the penicillin nucleus or at the 7-amino position of the cephalosporin nucleus is referred to as 'side chain', the corresponding acid as 'side chain acid'. The side chains of PenG, PenV and CefC are phenylacetyl, phenoxyacetyl and aminoadipyl, respectively. The side chains are removed by cleavage of an amide linkage (deacylation), resulting in 6-aminopenicillanic acid (6-APA) in case of the penicillin molecules and 7-aminocephalosporanic acid (7-ACA) in case of the cephalosporin molecule. In this respect also phenylacetyl-7-aminodesacetoxycephalosporanic acid (CefG) should be mentioned as a precursor of 7-ADCA, although CefG is not a fermentation product. CefG is usually produced chemically from Penicillin G.

In order to obtain β-lactam compounds with an altered activity spectrum, an increased resistance against β-lactamases or improved clinical performance of β-lactam compounds, 6-APA, 7-ACA and 7-ADCA are used as starting points for synthetic manipulation to produce the various penicillins and cephalosporins of choice. At present these semisynthetic penicillins and cephalosporins form by far the most important market of β-lactam antibiotics.

The production of semisynthetic β-lactam products requires the deacylation of the penicillins and cephalosporins produced from fermentation. Although rather efficient chemical routes are available for the deacylation (J. Verweij & E. de Vroom, Recl. Trav. Chim. Pays-Bas 112 (1993) 66–81), nowadays the enzymatic route is preferred in view of the high energy and solvents cost together with some environmental problems associated with the chemical route (Dunnill, P., Immobilised Cell and Enzyme Technology. Philos, Trans. R. Soc. London B290 (1980) 409–420). The enzymes which may accomplish the deacylation of β-lactam compounds are classified as hydrolases based on the chemical reaction they catalyse. However, those hydrolases which are particularly useful in the deacylation of β-lactam compounds are usually referred to in the art as 'acylases' or 'amidases'. These denominations as used in this specification have the same meaning. In connection with β-lactam antibiotics these acylases usually are further specified as 'β-lactam acylases' as not all amidases accept a β-lactam nucleus as an acceptor/donor moiety for the acyl group. According to the literature several types of β-lactam acylases may be envisaged, based on their substrate specificity and molecular structure (B. S. Deshpande et al., World J. Microbiology & Biotechnology 10 (1994) 129–138).

Acylase, Nomenclature & Classification
Classification according to specificity

The substrate specificity of the acylase is determined by a side chain binding pocket at the enzyme which recognizes the side chain moiety of β-lactam molecules. In general, the acylases are not very specific for the moiety adjacent to the nitrogen atom of the amide group (this might be a cephem group, a penem group, an amino acid, sugars, etc. (J. G. Shewale et al., Process Biochemistry International, June 1990, 97–103). In case of the Penicillin G acylases (Benzylpenicillin amidohydrolase, also named Penicillin amidase, EC 3.5.1.11) this acyl moiety must be very hydrophobic and is preferably phenylacetyl or (short) alkyl. Penicillin G acylase is used commercially to hydrolyse PenG or CefG to phenylacetic acid and 6-APA or 7-ADCA, respectively the most important intermediates for the industrial production of semi-synthetic penicillins and cephalosporins. Beside these major applications other have been reported for these enzymes such as blocking/deblocking of sensitive groups in organic synthesis and peptide chemistry, stereospecific conversions, optical resolution of phenylglycine, deesterification of carbinols, acylation of mono-bactams etc. In the various applications the enzyme may be used either in its native state or as immobilised preparation. Microbial whole cells containing the enzyme activity have also been used either as cell suspension or as immobilised cell preparation.

Examples of substrates which are not hydrolyzed by Penicillin G acylases are those with charged acyl moieties such as dicarboxylic acids: succinyl, glutaryl, adipyl and also amino-adipyl, the side-chain of CefC.

Penicillin V acylases are highly specific for phenoxyacetyl, while ampicillin acylase prefers D-phenylglycine as a side chain. Glutaryl-acylases deacylate glutaryl-7-ACA, which is prepared from CefC after enzymatic deamidation of the side chain with D-amino acid oxidase followed by chemical decarboxylation of the formed ketoadipyl derivative with peroxide, which is produced in the first step. Moreover some of these acylases have been reported to be capable of hydrolyzing cephalosporins (including the desacetoxy-derivative) with succinyl, glutaryl and adipyl as an acyl moiety and even in one case CefC to a very limited degree (for a review see EP-A-322032, Merck). So far these acylases have only been found in Pseudomonas species, and in certain strains of *Bacillus megaterium* and *Arthrobacter viscosus*.

Classification based on structural properties of the enzymes

Apart from their specificities acylases may also be classified based on molecular aspects (V. K. Sudhakaran et al., Process Biochemistry 27 (1992) 131–143):

Type-I acylases are specific for Penicillin V. These enzymes are composed of four identical subunits, each having a molecular weight of 35 kDa.

Type-II acylases all share a common molecular structure: these enzymes are heterodimers composed of a small subunit (α; 16–26 kDa) and a large subunit (β; 54–66 kDa). With respect to the substrate specificity, Type-II acylases may be further divided into two groups:
Type-IIA acylases comprise the Penicillin G acylases;
Type-IIB acylases comprise the Glutaryl acylases.

Type III acylases are the Ampicillin acylases which have been reported to be dimers consisting of two identical subunits with a molecular weight of 72 kDa.

Benefits of Protein Engineering with Respect to Screening/Chemical Modification

Enzymes with improved properties can be developed or found in several ways, for example, by classical screening methods, by chemical modification of existing proteins, or by using modern genetic and protein-engineering techniques.

Screening for organisms or microorganisms that display the desired enzymatic activity, can be performed, for example, by isolating and purifying the enzyme from a microorganism or from a culture supernatant of such microorganisms, determining its biochemical properties and checking whether these biochemical properties meet the demands for application. The present collection of acylases results from intensive screening programs. β-lactam acylase activity has been found in many microorganisms such as fungi, yeast, actinomycetes and bacteria.

If the identified enzyme cannot be obtained from its natural producing organism, recombinant-DNA techniques may be used to isolate the gene encoding the enzyme, express the gene in another organism, isolate and purify the expressed enzyme and test whether it is suitable for the intended application.

Modification of existing enzymes can be achieved inter alia by chemical modification methods. In general, these methods are too unspecific in that they modify all accessible residues with common side chains or they are dependent on the presence of suitable amino acids to be modified, and often they are unable to modify amino acids difficult to reach, unless the enzyme molecule is unfolded. In addition chemical modification require additional processing steps and chemicals to prepare the enzyme. Enzyme modification through mutagenesis of the encoding gene does not suffer from the problems mentioned above, and therefore is thought to be superior.

Moreover the choice for an acylase, subsequent construction and selection of high-yielding penicillin acylase-producing strains and the development of an industrial process for isolation and immobilisation, is a laborious process. In general for production and subsequent formulation of the mutants the wild type protocols can be followed. Therefore, once such a process has been developed successfully for a certain acylase it is very attractive to broaden the application of the acylase of choice instead of continuing the screening for enzymes from other sources. Therefore enzyme modification through mutagenesis of the encoding wild type gene is thought to be superior to screening especially when small adaptation of the properties of the enzyme are required. Desired properties may include altered specificity, altered specific activity for a certain substrate, altered pH dependence or altered stability. Mutagenesis can be achieved either by random mutagenesis or by site-directed mutagenesis.

Random mutagenesis, by treating whole microorganisms with chemical mutagens or with mutagenizing radiation, may of course result in modified enzymes, but then strong selection protocols are necessary to search for mutants having the desired properties. Higher probability of isolating desired mutant enzymes by random mutagenesis can be achieved by cloning the encoding enzyme, mutagenizing it in vitro or in vivo and expressing the encoded enzyme by recloning of the mutated gene in a suitable host cell. Also in this case suitable biological selection protocols must be available in order to select the desired mutant enzymes.

Site-directed mutagenesis (SDM) is the most specific way of obtaining modified enzymes, enabling specific substitution of one or more amino acids by any other desired amino acid.

The conversion of β-lactam intermediates to the desired semi-synthetic antibiotics may be performed chemically and enzymatically. If a suitable enzyme is available the enzymatic route is preferred because:

reactions can be performed stereospecifically;
reactants do not require side chain protection such as silylation;
less need for organic solvents, i.e. an organic solvent such as methylene chloride can be omitted which reduces environmental problems;
compared to the chemical route usually less steps are required;
neither extreme temperatures nor pressures required;
usually lower content of byproducts.

Synthetic manipulation to produce the various penicillins and cephalosporins of choice basically starts from 6-APA, 7-ACA and 7-ADCA, respectively.

The enzymatic conversion takes advantage of the fact that any enzymatic reaction is reversible, if the correct conditions are applied. The importance of such applications has been highlighted in previous reviews. The literature gives several examples of the application of penicillin acylases in biosynthetic routes (J. G. Shewale et al., Process Biochemistry International, June 1990, 97–103). Acyl derivatives of 6-APA, 7-ADCA, 7-ACA, 3-amino-4-α-methyl monobactamic acid and peptides have been prepared with side-chain moieties of varying structure. Besides 6-APA and 7-ADCA, penicillin acylase is used in the formation of antibiotic intermediates such as 6-amino-2,2-dimethyl-3-(tetrazol-5-yl) penam, methyl-6-aminopenicillate, 3-methyl-7-amino-3-cephem-4-carboxylic acid and 3-amino nocardic acid. The hydrolytic action is catalysed at alkaline pH (7.5–8.5) while at acidic or neutral pH (4.0–7.0) it promotes acylation reactions.

Various factors affect the performance of an acylase in bioconversion processes:

reaction medium: pH, ionic strength, temperature, organic solvents, etc.;
enzyme stability with respect to process conditions;
reactant stability;
catalytic activity of the enzyme.

Except reactant stability which is not an enzyme property, the other factors may be a target for enzyme modification via protein engineering.

Various of these factors have been explored in order to make biosynthesis processes economically viable. Methylesters which are superior acyl donors as compared to free acids of side chain acids have been used in the reaction. The equilibrium of the reaction has been shifted in favour of acylation by changing the water activity around the enzyme molecule with certain solvents. E.g. polyethyleneglycol, methanol, ethanol, propanol, butanol, and acetone are used in enhancing the yield of penicillin G, penicillin V and ampicillin.

Acylation reactions especially with 6-APA, 7-ADCA and 7-ACA generate antibiotics which are clinically important. However, the reaction needs to be monitored under strict kinetically controlled parameters. Although in some articles it was speculated that protein-engineering tools might be explored to obtain tailored enzyme molecules giving semi-synthetic penicillins and cephalosporins at a yield competing with existing chemical processes, there was no teaching whatsoever neither how this should be carried out, nor which enzymes should be engineered, or which amino acid residues should be substituted, nor any relation between the kind of substitution and the desired substrate.

The synthetic potential of a given penicillin acylase is limited due to the specificity of the enzyme. Therefore, there is a substantial interest in developing enzymes which are highly efficient in deacylation/acylation reactions to produce desired chemical entities. Of particular interest are the enzymatic deacylation of β-lactams (especially PenG, PenV, CefC, and derivatives thereof) to 6-APA and 7-ACA and derivatives, and the acylation of the latter compounds to produce semi-synthetic penicillins and cephalosporins of interest. In addition increased activity on more polar side chains or charged side chains such as succinyl, glutaryl or adipyl is desired. In particular, it is of major importance to dispose of an efficient enzyme which is capable of catalyzing the conversion of CefC (and derivatives) to 7-ACA (and derivatives).

Theoretical Aspects of the Application of Enzymes in Synthesis

Penicillin G acylases are hydrolases which catalyse the deacylation of various β-lactam compounds. Moreover as enzymes catalyse reactions in both directions, these acylases may also be used as a transferase to catalyse the synthesis of condensation products such as β-lactam antibiotics, peptides, oligosaccharides or glycerides. Enzyme catalysed synthesis may be carried out either as an equilibrium controlled or as a kinetically controlled reaction.

In an equilibrium controlled process the enzyme only accelerates the rate at which the thermodynamic equilibrium is established. The kinetic properties of the enzyme do not influence the equilibrium concentrations. However, the thermodynamic equilibrium is dependent on reaction conditions such as pH, temperature, ionic strength, or solvent composition. Often the conditions which favour the shift of the thermodynamic equilibrium in such a way that an optimal yield of the desired product is obtained are usually not optimal for the performance of the enzyme. In such cases enzyme engineering may be desired to adapt the enzymes to conditions which are closer to the thermodynamic optimum of the reaction. In this aspect properties such as stability, temperature optimum and pH optimum may be useful targets.

In kinetically controlled reactions conditions are chosen in such way that a considerable accumulation occurs of the desired product during the reaction under non-equilibrium conditions. In this case besides the already mentioned parameters also the kinetic properties of the enzyme are an important factor in obtaining yields which can compete favourably with existing chemical processes.

The kinetics of Penicillin G acylases are consistent with catalysis proceeding via an acyl-enzyme intermediate. This intermediate plays a key role in the enzyme mechanism as is depicted in FIG. 1. In this scheme the acylase acts as a hydrolase where the acyl group is transferred to water, or as a transferase where the acyl transfer from an activated substrate to a nucleophile is catalyzed. The chemical entities are represented by general formulas. The nature of the chemical entities X and Y in compound X—CO—NH—Y which are accepted as a substrate by a particular acylase is determined by the specificity of that acylase. X represents the side chain, while Y represents the acyl acceptor group. For instance, for the deacylation of PenG, X—CO— represents the phenylacetyl side chain and —NH—Y represents 6-aminopenicillic acid. Given a certain enzymatic mechanism the specificity is determined by the architecture and the amino acid composition of the binding sites for X and Y.

In the first step of the mechanism, the substrate binds to the enzyme to form the non-covalent Michaelis-Menten complex. In the subsequent step, the covalent intermediate is formed between the enzyme and the acyl moiety of the substrate (E—CO—X). Formation of the acyl-enzyme may occur through cleavage of an amide bond (amide hydrolysis of X—CO—NH—Y) or an ester bond (ester hydrolysis X—CO—O—R) and at low pH it may also be formed directly from X—COOH. The nucleophile YNH binds to the acyl-enzyme before deacylation. Under conditions which favour the deacylation (the enzyme acts as a deacylase or amidase) a water molecule will hydrolyse the acyl enzyme thereby liberating the second product X—COOH and regenerating the enzyme for a new catalytic cycle. Under conditions which favour formation of compound X—CO—NH—Y, the nucleophile Y—NH reacts with the acyl enzyme instead of water (aminolysis). For PenG the mechanism above was confirmed by the observations that phenylacetic acid acts as a competitive inhibitor and 6-APA as a non-competitive one.

In general the formation of the acyl-enzyme from amides ($v_1$) is slow compared to the hydrolysis of the acyl enzyme ($v_3$). However, when the appropriate ester derivatives of the side chain are used (X—CO—O—R) or just the amide (X—CO—NH2) then the formation of the acyl-enzyme ($v_2$) is relatively fast in comparison with hydrolysis ($v_3$). The consequence is that the acyl enzyme intermediate will accumulate. In the presence of suitable compounds with a free primary amino group (general representation Y—NH2) such as, for example, 6-APA, 7-ACA, 7-ADCA which are bound by the acylase, an amide bond may be formed giving X—CO—N—Y ($v_{-1}$, aminolysis).

With respect to the preference for chemical entities X and Y substitution of residues in the binding sites for X and Y at the enzyme alter this preference. Changes in substrate specificity include all combinations of increase and decrease of $V_{max}$ and $K_m$. In some cases a more specific enzyme is required, e.g. with mixtures of enantiomers it may be useful when the enzyme is selective for only one of the enantiomers. In other cases, e.g. the conversion of rather pure compounds, a higher conversion rate might be preferred at the cost of selectivety. At high substrate concentrations a higher $V_{max}$ is preferred while Km is less important.

Acylases used for substrate activation and kinetically controlled synthesis may be altered in such a way that their catalytic ability to hydrolyse compounds ($V_3$=transfer acyl group to water) has been suppressed with respect to acyl transfer to a non-aqueous acceptor nucleophile ($v_{-1}$); ratio $V_{-1}/v_3$ increased relative to wild type.

The ratio of transferase to hydrolase activity is the enzyme property that influences yield in kinetically controlled synthesis of condensation products. The ratio of the apparent second order rate constants for the acyl transfer to YNH or H20 can be determined from the initial rates of formation of X—CO—NH—Y and X—COOH from the acyl-enzyme.

Transferase activity may be improved by improving the affinity of the nucleophile for the enzyme-acyl complex with respect to water. As the transfer of the acyl group ($v_{-1}$) is proportional to amount of nucleophile bound to the acyl-enzyme an increased affinity for the enzyme-acyl complex will improve the yield of the condensation product with respect to hydrolysis.

In addition a higher yield in an enzyme catalysed biosynthesis may be obtained by reducing the hydrolysis of the desired products ($v_1v_3$). Variants for which the hydrolysis of amide bonds relative to ester bonds has been decreased are still able to form the acyl enzyme from ester substrates ($v_2$) but have relatively weak hydrolysis activity for the product amide bond (increased ratio $V_1/V_2$ with respect to wild type).

Relevant Literature

Several genes encoding Type-IIA Penicillin G acylases have been sequenced, viz. the genes from *E. coli* (G. Schumacher et al., Nucleic Acids Research 14 (1986) 5713–5727), *Kluyvera citrophila* (J. L. Barbero et al., Gene 49 (1986) 69–80), *Alcaligenes faecalis* (U.S. Pat. No. 5,168, 048, Gist-brocades), *Providencia rettgeri* (G. Ljubijankic et al., J. DNA Sequencing and Mapping 3 (1992) 195–201) and *Arthrobacter viscosis* (M. Konstantinovic et al., (1993) EMBL databank entry L04471).

The use of recombinant DNA methods has enabled an increase of the production levels of commercially used penicillin acylases (Mayer et al., Adv.Biotechnol. 1 (1982) 83–86) and has enlarged the insight into the processing of these enzymes (G. Schumacher et al., Nucleic Acids Research 14 (1986) 5713–5727). The penicillin acylase of *E. coli* was found to be produced as a large precursor protein, which was further processed into the periplasmic mature protein constituting a small ($\alpha$) and a large ($\beta$) subunit. Cloning and sequencing of the *Kluyvera citrophila* acylase gene has revealed a close homology with the *E. coli* acylase gene (J. L. Barbero et al., Gene 49 (1986) 69–80). Also for *Proteus rettgeri* (G. O. Daumy et al., J. Bacteriol. 163 (1985) 1279–1281) and *Alcaligenes faecalis* (U.S. Pat. No. 5,168, 048 and EP-A-453048, Gist-brocades) Penicillin G acylase a small and a large subunit has been described.

These publications neither teach nor suggest the instant invention.

Redesigning of specific activity of enzymes with the aid of protein-engineering techniques has been described.

Patent applications EP-A-130756 and EP-A-251446 describe the selection of residues and the mutagenesis of some of these residues in a certain group of serine protease with the purpose to alter the kinetic properties of these enzymes.

As these patent applications specifically deal with a certain type of serine proteases (the subtilisin type), these publications do not indicate which residues modulate the catalytic properties of Type-IIa Penicillin G acylases.

Wells et al. (Proc. Natl. Acad. Sci. USA 84 (1987) 5167) show an example for subtilisin. *Bacillus licheniformis* and *B. amyloliquefaciens* serine protease differ by 31% (86 residues) in protein sequence and by a factor of 60 in catalytic efficiency on certain substrates. By substituting 3 of the 86 different amino acids from the *B. amyloliquefaciens* sequence by the corresponding *B. licheniformis* residues the catalytic activity of the mutant enzyme was improved nearly 60 fold.

Wilks et al. (Science 242 (1988) 1541) describe how a lactate dehydrogenase was changed into a malate dehydrogenase by mutating glutamine 102 into arginine 102. In both cases, serine protease and lactate dehydrogenase, the inspiration for the modification proposal came from comparison with naturally occurring enzymes, which already showed the desired specificity. In the same way the specificity of cytochrome p450$_{15\alpha}$ was changed into the specificity of cytochrome p450$_{coh}$ by replacing Leu209 with Phe209 (Lindberg and Negishi, Nature 339 (1989) 632).

Patent application WO93/15208 describes a method for modifying the specificity and or efficiency of a dehydrogenase while retaining its catalytic activity, characterized in that it comprises: selecting an enzyme, the tertiary structure of which is substantially known or deduced; identifying at least one specificity and/or efficiency-related region; identifying or constructing unique restriction sites bounding the identified region in the DNA encoding therefor; generating a DNA sequence which corresponds to at least a portion of the identified region, except that the nucleotides of at least one codon are randomized, or selecting as a substitute for at least a portion of the identified region an alternative such region, which may itself be similarly randomized; using the generated or substitute DNA sequence to replace the original sequence; expressing the DNA including the generated or substitute DNA sequence; and selecting for a desired modification so that the DNA coding therefor may be isolated. As dehydrogenases are in no way related to Penicillin G acylase, this patent application does not reveal the residues in the acylase which should be substituted to alter its kinetic properties.

Forney et al. (Appl. and Environm. Microbiology 5 (1989) 2550–2556; Appl. and Environm. Microbiology 55 (1989) 2556–2560) have isolated by cloning and in vitro chemical/UV random mutagenesis techniques *E. coli* strains capable of growing on glutaryl-L-leucine or D(-)-$\alpha$-aminophenyl-acetyl-(L)-leucine. Penicillin acylase produced by the mutants hydrolyse glutaryl-L-leucine between pH 5 and 6 or D(-)-$\alpha$-amino-phenyl-acetyl-(L)-leucine at pH 6.5. Although it is supposed that the specificity shift of the Penicillin G acylase is due to one or more mutations in the acylase, the residue(s) involved nor the kind of mutation(s) were identified.

J. A. Williams & T. J. Zuzel (Journ. of Cell. Biochem. (1985) supplement 9B, 99) reported in an abstract of a poster presentation the modification of the substrate specificity of Penicillin G acylase by in vitro mutagenesis of a methionine. Although the abstract does not report the position of this methionine, from the poster it seemed to be possible to conclude that it involved position Met168 in *E. coli* acylase. However, this work did not reveal any details how substitution of this methionine relates to the observed specificity change. Prieto et al. (I. Prieto et al., Appl. Microbiol. Biotechnol. 33 (1990) 553–559) replaced Met168 in *K. citrophila* for Ala, Val, Asp, Asn, Tyr which affected the kinetic parameters for PenG and PenV deacylation. In addition mutants Lys375Asn and His481Tyr were made which showed hardly any effect on $k_{cat}$/Km.

J. Martin et al. analysed mutant Met168Ala in *K. citrophila* penicillin acylase and reported altered kinetic properties. (J. Martin & I. Prieto, Biochimica et Biophysica Acta 1037 (1990), 133–139). These references indicate the importance of the residue at position 168 in *E. coli* and *K. citrophila* for the specificity with respect to the acyl moiety. However, this work did not reveal any details how substitution of this methionine relates to the specificity change for the conversion of a desired substrate.

Wang Min reported mutagenesis of Ser177 in *E. coli* Penicillin G acylase to Gly, Thr, Leu, Arg but failed to obtain active acylases. (Wang Min et al., Shiyan Shengwu Xuebao 24 (1991), 1, 51–54).

Kyeong Sook Choi et al. (J. of Bacteriology 174 (1992) 19, 6270–6276) replaced the $\beta$-subunit N-terminal serine in *E. coli* penicillin acylase by threonine, arginine, glycine and cysteine. Only when the N-terminal residue was cysteine the enzyme was processed properly and a mature enzyme but inactive enzyme was obtained. In addition chemical mutagenesis of the $\beta$-subunit N-terminal serine also led to severe/almost complete loss of activity (Slade et al., Eur. J. Biochem. 197 (1991) 75–80; J. Martin et al., Biochem. J. 280 (1991) 659–662).

Sizman et al. (Eur. J. Biochem. 192 (1990) 143–151) substituted serine 838 in *E. coli* for cysteine without any effect on the post-translational processing nor on the catalytic activity of the enzyme. In addition Sizman et al. made various deletion mutants of penicillin acylase. It showed that correct maturation of the acylase is very sensitive to mutagenesis. All β-subunit C-terminal deletion mutants were not expressed except for the mutant lacking the last three residues which, however, was very unstable. Insertion of four residues in *E. coli* at position 827 also failed to give active enzyme.

Prieto et al. replaced glycine 310 in *Kluyvera citrophila* penicillin acylase for glutamic acid. However, no active enzyme was obtained.

In EP-A-453048 it has been described how protein engineering may be used to alter the specificity of Type-IIa as well as Type-IIb acylase. However, the applied procedures are limited to the generation of libraries of randomly generated acylase mutants which have to be screened for a desired activity. Although by the method described in that patent application the number of amino acid positions which may be mutated has been reduced, the number of remaining positions is still large, so that position directed mutagenesis would be a laborious job. The present invention, however, gives a much more limited number of positions which are to be mutated. In addition amino acids at these positions are in direct contact with the substrate, which means that substitution will affect interaction with the substrate directly. Moreover the procedure leading to the present invention allows one to choose a particular amino acid substitution in order to obtain a desired effect for a specific substrate.

SUMMARY OF THE INVENTION

The present invention provides an isolated mutant prokaryotic Penicillin G acylase or its preenzyme or preproenzyme comprising:

a substitution at one or more selected sites of the positions corresponding to A139 to A152, B20 to B27, B31, B32, B49 to B52, B56, B57, B65 to B72, B154 to B157, B173 to B179, B239 to B241, B250 to B263, B379 to B387, B390, B455, B474 to B480 in *Alcaligenes faecalis* Penicillin G acylase or its pre- or preproenzyme; and an altered substrate specificity or altered specific activity relative to the corresponding wild-type unsubstituted Penicillin G acylase.

Preferably, said isolated mutant prokaryotic Penicillin G acylase is originated from *Alcaligenes faecalis*.

Furthermore a nucleic acid sequence encoding said mutant acylase, a vector which comprises said nucleic acid sequence, and a microorganism host strain transformed with said vector have been provided for by the present invention.

According to another aspect of the invention a process of preparing said isolated mutant Penicillin G acylase has been provided, which process comprises:

culturing a microorganism host strain transformed with an expression vector comprising a nucleic acid sequence encoding a mutant acylase enzyme as defined above, whereby said mutant acylase is produced; and isolating said acylase.

Finally, a method for conducting an acylation or deacylation reaction has been provided, said process comprising contacting said isolated mutant Penicillin G acylase with a substrate for said acylase under conditions suitable for said reaction to occur. Preferably, a β-lactam compound is produced by said process.

Especially, a method for deacylating an acylated 6-amino penicillanic acid, an acylated 7-amino(desacetoxy) cefalosporanic acid or a salt or ester thereof to form the corresponding 6-amino penicillanic acid or 7-amino (desacetoxy)cefalosporanic acid or salt or ester thereof, respectively, which comprises contacting said 6-acylated or 7-acylated compound with a mutant acylase as defined above under conditions suitable for deacylation to occur, and a method for producing a semi-synthetic acylated 6-amino penicillanic acid, an acylated 7-amino(desacetoxy) cefalosporanic acid or a salt or ester thereof which comprises contacting a corresponding 6-amino or 7-amino β-lactam and an acylating agents with a mutant acylase as defined above under conditions suitable for acylation to occur, has been provided for.

BRIEF DESCRIPTION OF THE DRAWINGS

FIG. 2: Alignment of α (2a) (FIGS. 2A–2B) and β (2b) (FIGS. 2C–2F) subunit of Type-IIa penicillin acylases mature enzymes. *Alcaligenes faecalis* (afae), *E. coli* (ecol), *Kluyvera citrophila* (kcit), *Arthrobacter viscosis* (avis), *Providencia rettgeri* (pret). Chain identifier A and B for α and β chain, respectively. An asterix denotes that the sequence contains the same amino acid at that position as the sequence from the *A. faecalis* acylase. For the *Providencia rettgeri* acylase the N-terminus and the C-terminus of the α-subunit not known. N-terminus β subunit *Providencia rettgeri* based on alignment with other acylases.

DETAILED DESCRIPTION OF THE INVENTION

Hydrolysis/deacylation

Figure 1:
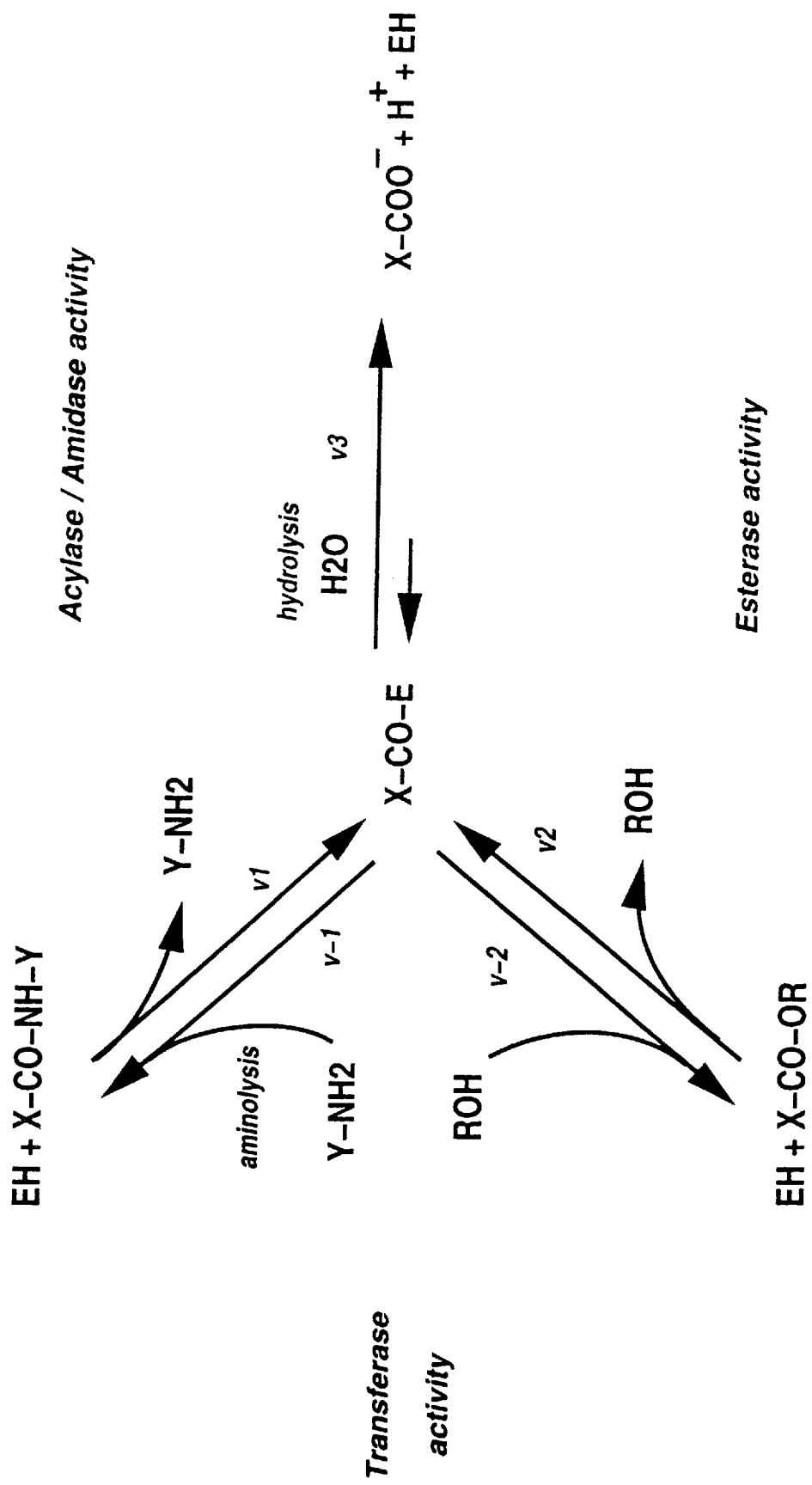
FIG. 1: Reaction scheme for Type-IIa penicillin acylases catalysed conversions. EH represents the enzyme where H stands for the proton which is transferred to the leaving group. X stands for the acyl moiety or side chain. Y is the compound to be acylated (acylation) or to be deacylated (deacylation). Compound X—CO—OR may also be a simple amide X—CO—NH2.

The present invention relates to the identification of residues which alter the kinetic properties of Penicillin G acylase, whereby said resulting Penicillin G acylase variant is more useful than said precursor Penicillin G acylase for the deacylation of primary aminogroups such as, for example, occur in penicillins and cephalosporins. These kinetic properties comprise specific activity, pH dependence of kinetic parameters, substrate specificity, stereo-selectivity and the ratio transferase to hydrolase activity.

Synthesis/acylation

The present invention relates to Penicillin G acylase variants derived from precursor Penicillin G acylases via recombinant DNA methodology by changing at least one amino acid residue in said precursor, said Penicillin G acylase variant being more useful than said precursor Penicillin G acylase for the acylation of primary amino groups such as, for example, occur in β-lactam nuclei (preparation of semi-synthetic β-lactam compounds) and peptides.

The present invention relates to Penicillin G acylase variants derived from precursor Penicillin G acylases via recombinant DNA methodology by changing at least one amino acid residues in said precursor, said Penicillin G acylase variant being characterized by having a higher ratio transferase to hydrolase activity than said precursor Penicillin G acylase.

The Penicillin G acylases which are subject of this invention:
- are isolated from prokaryotes;
- are transcribed as a single peptide chain precursor;
- are processed intracellularly after transcription resulting in a heterodimer with a small N-terminal domain (the α-domain) and a larger C-terminal domain (the β-chain). The molecular weight of the N-terminal domain is in the range 16–28 kDa. The molecular weight of the C-terminal domain is in the range 54–68 kDa;
- may occur in solution as multimers of the αβ heterodimers;
- have a serine at the N-terminus of the β-subunit.

Examples of such acylase producing microorganisms are certain strains of the species *Escherichia coli, Kluyvera citrophila, Providencia rettgeri*, Pseudomonas sp., *Alcaligenes faecalis, Bacillus megaterium*, and *Arthrobacter viscosus*.

Several genes encoding Penicillin G acylases have been sequenced, viz. the genes from *E. coli, Kluyvera citrophila Alcaligenes faecalis, Proteus rettgeri* and *Arthrobacter viscosis*.

The alteration of the substrate specificity of Penicillin G acylases is achieved in such a way that the mutant enzymes are able to cleave or synthesize penicillin and cephalosporin derivatives possessing side-chains other than phenylacetyl, which is the natural side-chain of penicillin G. Examples of side-chains which are presently not significantly affected by Penicillin G acylases are acyl groups derived from the dicarboxylic acids succinic acid, glutaric acid, adipic acid and aminoadipic acid (the latter being the natural side-chain of CefC).

In another aspect the alteration of the specificity and activity of Penicillin G acylases is performed for side-chains which are already existing substrates for the said acylases. Using protein engineering the affinity for a substrate can be altered (e.g. increased, expressed by a lower $K_m$ for said substrate), the catalytic turnover may be altered (e.g. increased, expressed by a higher $k_{cat}$ for said substrate) or the second order rate constant may be altered (e.g. expressed by an altered $k_{cat}$/Km ratio, a parameter which is usually used to compare specificity of an enzyme for different substrates). Relevant substrates in this aspect include acylated β-lactam derivatives such as penicillin V (PenV), ampicillin, amoxicillin, cefalexin, cefadroxyl or cefaclor. Moreover alteration of kinetic properties with respect to simple amides and esters of the acyl moiety are useful for obtaining increased accumulation of the acyl enzyme intermediate which may improve the yield in biosynthesis processes.

In another aspect the alteration of the specificity and activity of Penicillin G acylases is performed in order to increase the stereo specificity of Penicillin G acylases which results in enzymes which show improved enantiomeric excess in conversions with racemic mixtures of chiral compounds. Such property makes the Penicillin G acylase extremely useful for synthesis of enantiomerically pure semisynthetic antibiotics from racemic mixtures of phenylacetyl side chains or activated derivatives of the phenylacetyl side chains (e.g. phenylglycine-amides or esters therefrom, p-hydroxyphenylglycine-amides or esters therefrom, etc.) containing a chiral α-carbon due to the presence of an amino group (e.g. ampicillin, cefalexin, amoxicillin, cefadroxyl, cefaclor) or a hydroxyl group (cefamandol).

Apart from stereoselectivity for the acyl Cα position Penicillin G acylase exhibits also stereoselectivity for the amino part of the substrate. In case of amino acids the acylase requires the L-configuration at the Cα atom. In another aspect of the invention steroselectivity of the enzyme for the amino part of the substrate may be altered.

In another aspect of the invention the product inhibition is reduced with respect to the wild type enzyme. The desired variant maintains its initial high deacylation rate for a longer period during conversion resulting in a higher productivity. Examples of such inhibitory products are phenylacetate, phenoxyacetate, phenylglycine, p-hydroxyphenylglycine etc.

In another aspect of the invention the transferase activity of the enzyme is improved with respect to the hydrolases activity which makes the enzyme more useful in biosynthetic conversions. In particular variants with improved performance in the enzymatic synthesis of amoxicillin, ampicillin, cefaclor, cefadroxil, cefprozil, cephalexin, and cephradine are preferred embodiments.

Compared to the precursor acylase desired variants for biosynthesis are more easily deacylated by a β-lactam nucleus than by water (ratio aminolysis/hydrolysis). This may be obtained by improving the binding of the nucleophile relative to water. Desired variants have altered esterase/amidase ratio for particular substrates relative to the precursor enzyme i.e. for certain side chains the desired enzyme shows a decreased amidase activity for amide derivatives of those side chains compared to the esterase activity for esters of the corresponding side chains.

In order to achieve alterations in the enzyme molecule, it is highly desirable to avail of the 3D structure of said enzyme. Sofar, no high-resolution, 3D-structures of acylases have been published.

The known Penicillin G acylase gene sequence derived amino acid sequences were aligned in such a way that optimal homology was obtained. For sequence alignment the types of amino acids may be suitably used as parameters, based on identity but also on similarity. For example, serine is similar to threonine, aspartic acid is similar to glutamic acid, etc. The results are shown in FIG. 2 which gives an alignment of Penicillin G acylases from *Escherichia coli, Kluyvera citrophila, Alcaligenes faecalis, Providencia rettgeri* and *Arthrobacter viscosis*. The alignment of the five amino acid sequences reveals a significant homology between the Penicillin G acylases which points to a similar 3D-structure.

In an embodiment of the invention corresponding positions of other Penicillin G acylases, which are structurally homologous to *Alcaligenes faecalis* Penicillin G acylase can be substituted in the same way as *Alcaligenes faecalis* at the positions which are homologous to the positions in *Alcali-* genes faecalis Penicillin G acylase. The corresponding positions for these proteases may be obtained from the amino acid alignment as depicted in FIG. 2. In FIG. 2 the amino acid sequence of various acylases have been aligned, with respect to the sequence of the acylase of *Alcaligenes faecalis* (*A.fae*).

Although the selection of residues will be demonstrated here using the specific example of *Alcaligenes faecalis* Penicillin G acylase it is clear that due to homology similar substitution sites can be selected in Penicillin G acylases obtained from other species. The approach described would give rise, after amino acid replacement at corresponding positions in the Penicillin G acylase from the other species, to similar altered kinetic properties of other Penicillin G acylase also. By similar is meant the kind of effect which the substitutions have on the kinetic parameters change.

In an embodiment of the invention genes encoding known Penicillin G acylases, for example, Penicillin G acylases from *Escherichia coli, Kluyvera citrophila, Alcaligenes faecalis, Providencia rettgeri* and *Arthrobacter viscosis* or any other organism producing such enzymes, are mutated in such a way that the enzymes obtain an altered specificity for their substrates.

In an embodiment of the invention, genes encoding the structurally homologous Penicillin G acylases, for example, Penicillin G acylases from *Escherichia coli, Kluyvera citrophila, Alcaligenes faecalis, Providencia rettgeri* and *Arthrobacter viscosis*, are mutated in such a way that the enzymes obtain an altered substrate specificity or new specificity.

Changes in substrate specificity demonstrated in the present invention include all combinations of increase and decrease of $V_{max}$ and $K_m$ for both penicillin and cephalosporin derivatives. A person skilled in the art will understand that this encompasses the changes in other kinetic parameters. Furthermore, the specificities for other substrate will inherently be changed also. The proposed rules for changing the substrate specificity are not restricted to the mentioned substrates, they can be applied to other substrates among these are phenylacetyl or phenoxyacetyl derivatives of amino acids, aminoalkylphosphonic acids, primary and secondary alcohols, cefamicines, nocardicines, monobactams, nucleic acids, carbohydrates, peptides.

As the mechanism of maturation of Penicillin G acylase from a one-peptide chain to an active dimer is still obscure another important aspect of the invention shows that it is possible to replace active site residues in Penicillin G acylase without affecting the maturation of the acylase.

The underlying invention to provides a methods to recruit novel specificities for Type-IIa Penicillin G acylases. For the introduction of point mutations a rational approach is taken, relying on the application of protein crystallography, molecular modelling and computational methods, enzymology and kinetics, molecular biology and protein chemistry techniques. The strategies for the identification of targeted mutations in Penicillin G acylase are innovative in a sense that it is recognized that point mutations may affect several different properties of the protein structure at once. In particular some point mutations may prevent proper folding or correct processing resulting in an inactive enzyme. Therefore, although the described strategies make use of well established structure-function relationships, they also provide a rational way to avoid or correct unwanted alterations of secondary properties.

According to the present invention specific amino acid positions to be substituted have been identified within the available 753 positions in the Penicillin G acylase molecule from *A. faecalis*, and the effect of such mutations on the particular properties of the enzyme. Thus A139 to A152 [SEQ ID NO:27], and B1, B2, B20 to B27, B31, B32, B49 to B52, B56, B57, B65 to B72, B154 to B157, B173 to B179, B239 to B241, B250 to B263, B379 to B387, B390, B455, and B474 to B480 [SEQ ID NO:32] are identified as important positions with regard to the catalytic properties of the enzyme. Various specific residues have been identified as being important with regard to substrate specificity. These residues include: A:Met143, A:Arg146, A:Phe147, A:Thr150 [SEQ ID NO:27], and B:Pro22, B:Phe24, B:Gly25, B:Tyr27, B:Tyr31, B:Thr32, B:Pro49, B:Tyr52, B:Leu56, B:Phe57, B:Gly66, B:Ala67, B:Thr68, B:Ala69, B:Gly70, B:Pro71, B:Trp154, B:Val157, B:Met173, B:Ile175, B:Ser176, B:Ile177, B:Trp179, B:Asn239, B:Trp240, B:Thr251, B:Thr253, B:Tyr254, B:Tyr255, B:Trp256, B:Arg261, B:Met262, B:Asn379, B:Pro380, B:Gly381, B:Ser382, B:Ile383, B:Asn384, B:Lys390, B:Phe455 B:Thr477, and B:Glu478 [SEQ ID NO:32]. The identification of these positions, including those yet to be mutated is based on a 3D model of the *A. faecalis* Penicillin G acylase (see FIGS. 4a and 4b).

Selection Procedure for Residues which Alter Desired Properties. Desired Properties are Altered Catalytic Properties, Altered Specificity, Improved Transferase Activity The crucial first step for performing site-directed mutagenesis with the object to alter kinetic properties of an enzyme is to obtain a 3D structural model of the subject Penicillin G acylase complexed with the β-lactam compound of interest. This can be done in two ways, namely via a direct experimental approach, or via an indirect approach using molecular modeling.

The direct approach

Determine the 3D-structure of the subject Penicillin G acylase in complex with the β-lactam compound of interest by X-ray diffraction. However, when the particular β-lactam compound is a substrate for the particular Penicillin G acylase, it will be converted into the products of the reaction in the time-course of the structure determination experiment. In such cases cryo-crystallography may be applied or very fast data-collection techniques such as Laue diffraction. With conventional techniques binding of fragments of the substrate can reveal the binding site. As an alternative the substrate can be modified in such a way that the scissile bond in the substrate cannot be cleaved by the enzyme (e.g. phosphoamide or phosphonate bonds instead of a peptide bond in a peptide, D. E. Tronrud et al. Science 235 (1987) 571–574). However, an elegant method is to replace one or more of the catalytic residues resulting in an inactive enzyme which cannot convert the substrate but can still bind the substrate. For example, in Penicillin G acylase the β-subunit N-terminal serine may be mutated to cysteine. When it is not possible to obtain a 3D structure of the subject acylase complexed with the desired β-lactam derivate by experiment, conventional computer modelling techniques can be applied. Chemical modification studies and site directed mutagenesis revealed the N-terminal serine of the β-subunit to be critical for catalytic activity. Surprisingly calculation of the accessible residues in *A. faecalis* Penicillin G acylase model revealed a deep hydrofobic cavity near the β-subunit N-terminal serine which accommodates the Penicillin G phenylacetyl side chain perfectly while positioning the β-subunit N-terminal serine in an ideal position for nucleophilic attack at the peptide carbonyl of PenG.

In the next step the β-lactam moiety was positioned while keeping the phenylacetyl group fixed in its binding pocket.

Atomic overlap between substrate and enzyme is avoided as much as possible while positive interactions are maximized. Relevant positive interactions which contribute to binding are hydrogen bonding, electrostatic interactions and favourable VanderWaals contacts. The contribution of hydrofobic interactions can be estimated from the calculation of the accessible non-polar surface which is buried by binding the substrate to the enzyme.

In addition to manual manipulation of the substrate computational techniques are applied to optimize the substrate-enzyme complex. Molecular mechanics techniques such as energy minimization and molecular dynamics are very useful. Suitable forcefields for proteins such as CVFF, AMBER, CHROMOS may be used.

The final model is used to survey the environment of the PenG molecule. This survey supplies crucial insight in the residues which interact with the PenG molecule (see example 1). In addition it provides insight which residues interact with which parts of the substrate. This information provides the molecular biologist with only a limited set of residues compared to the overall size of the acylase (753 residues) which can be used to modulate the catalytic properties of Penicillin G acylase. Now a person skilled in the art of site specific mutagenesis just has to focus on only a limited number of residues, substitute these residues and select for desired altered catalytic properties.

In general when a substrate binds to the free enzyme it causes some strain in the enzyme and in the substrate. Such strain can be relieved by molecular mechanics calculations allowing atoms to shift position with respect to each other. Comparison of the enzyme-substrate complex with the free enzyme will indicate which residues are affected most by substrate binding. Parameters which are important in this aspect are RMS positional shifts of residues with respect to the free enzyme, changes in the electrostatic environment around residues with respect to the free enzyme, hydrogen bond formation or the change of free energy of residues. Electrostatic potentials may be calculated using a program such as DELPHI (Biosym Technologies). As residues which are affected by binding of the substrate will in turn affect the binding of the substrate, substitution of these residues is a preferred embodiment of this invention taking into account the restrictions for substitution of amino acids in proteins structures. Substitution that should be avoided are those substitutions which are expected to affect typical structural arrangements such as: salt bridges, packing of helices, stabilization of helices by keeping a negative charge at the start of a helix, initiation of helices, e.g. prolines at the start of a helix, Phi-psi angles which are outside the allowed region for the residue that is going to be inserted.

The proposed rules for changing the activity for a certain substrate are not restricted to PenG, they can be applied to other substrates as well. For example, instead of PenG a cephalosporin molecule may be taken such as CefG, which has the phenylacetyl side chain in common with PenG. In this case the whole modelling procedure may be repeated as described above. However, we prefer to substitute in the computer the 6-APA moiety of the PenG molecule which is complexed to the Penicillin acylase for the 7-ADCA moiety and subsequently refine the structure by molecular mechanics. Comparison of the structures of Penicillin G-acylase complex with the CefG-acylase complex will establish the residues which have been affected by modification of the substrate. Residues which are affected by modification of PenG will in turn modulate the binding of the modified substrate. Substitution of such residues is a preferred embodiment in order to alter the kinetic properties of such a modified substrate with respect to PenG.

For some modifications of the substrate it turns out to be impossible to relieve the strain caused by the modification without effecting the position of the scissile peptide bond with respect to the β-subunit N-terminal serine nucleophile. In such cases the distance from the β-subunit N-terminal serine nucleophile to the carboxyl carbon of the scissile bond is constrained within the range 2 to 3 Å during energy minimization and molecular dynamics. In addition computational mutagenesis of the acylase is performed to reduce undesirable interaction with the substrate and increase beneficial interaction (relevant interactions have been discussed above). However, when the binding of the modified substrate is unwanted and should be prohibited, undesirable interaction may even be increased at such positions by site directed mutagenesis. This approach establishes a limited number of mutations which will alter the kinetic properties in a desired direction. Subsequently such limited number of mutations can be made and tested for the desired properties.

Desired modifications imply substitution of the PenG side chain benzene ring by a five- or six-membered hydrocarbon ring (e.g. cyclohexadienyl, cyclohexenyl, cyclohexyl), optionally substituted either by a five-membered heterocycle containing one to four heteroatoms (N, O, or S) (e.g. thienyl, furyl) which heterocycle may be optionally substituted, or by an aliphatic side chain (e.g. propyl, butyl, pentyl, heptyl) which may be optionally substituted. Side chains may have one or more substituent including but not limited to hydroxyl, halogen, alkyl, alkoxyl, carboxyl, nitro, amino, and the like. In addition the phenylacetyl side chain may be substituted at the α-position resulting in a D- or L-stereoisomer. Substituent may include but are not limited to hydroxyl, halogen, alkyl, alkoxyl, carboxyl, nitro, amino, and the like. Selecting residues which affect the selectivity of the acylase with respect to stereoisomers is a preferred embodiment of the invention. Examples of desired side chains are, for example, 2-thienylacetyl, α-hydroxyphenylacetyl, p-hydroxyphenylacetyl, p-hydroxyphenylglycyl, phenylglycyl, succinyl, glutaryl, adipyl, α-aminoadipyl etc.

Beside modification of the β-lactam side chain also the β-lactam moiety itself may be subject to modification. As exemplified above the 6-APA moiety may be replaced by 7-ADCA. Instead 7-ACA may be taken. In addition the β-lactam moieties may be substituted at one or more positions. In particular the cephalosporins may contain substituents at the sulphur, at the 3-position or at the 4 position. For example, the 3-position may be substituted with a halogen atom, a methoxy, a methyl or a methylene bonded via a bridging atom O, N, or S to an organic moiety or five- or six membered (hetero) cyclic group which may optionally be substituted. At the 4-position the carboxylic acid substituent may be modified with various carboxyl protecting groups. Furthermore the given method allows also to analyze the structural requirements for acylases which may convert β-lactam moieties such as carbapenems, nocarcidines, monobactams or derivatives derived therefrom.

For the purpose of biosynthesis the interaction of the acylase with reactive derivatives of desired side chains may be modulated. Useful examples of such side chain derivatives are alkyl esters, amides and acylated amino acids.

The process of the invention can be used to select those position in type-II Penicillin G acylases at which amino acids should be substituted in order to affect the interaction with penicillins/cephalosporins and their derivatives which results in enzymes with altered kinetic properties. Position directed mutagenesis will provide a limited number of variants which can be easily tested for improved conversion of the desired substrate. This in contradiction to the random approach which results in an enormous number of mutants which is very difficult to handle.

Materials and Methods

Mutagenesis

For the construction of mutant acylase genes the overlap extension polymerase chain reaction has been used essentially as described by Ho et al. (Gene 77 (1989) 51–59). Mutant oligo's were used in combination with flanking oligo's to generate DNA amplification products harbouring the desired mutation. This mutant DNA fragment was exchanged with a corresponding restriction fragment of the wild type gene, e.g. pMcAF. The mutant oligo's have been designed to harbour single and multiple mutations.

Site-directed mutagenesis of cloned DNA fragments can also be carried out as described by Stanssens (Stanssen et al., Nucleic Acids Res. 17 (1989) 4441–4454) with the aid of the phasmid pMa/c system. Suitable gapped duplex molecules of acylase genes were constructed. With specific mismatch oligonucleotides site directed mutations were introduced. Expression of acylase genes was obtained in E. coli WK6 either from the homologous expression signals or from the E. coli lac, tac or trp promoter (De Boer et al., Proc. Natl. Acad. Sci. USA 80 (1983) 21–25). 'Spiked' oligo mutagenesis and random mutagenesis of the gapped DNA was performed as described (EP-453048).

Both PCR overlap extension and gapped duplex have been combined with another type of mutagenesis: targeted random mutagenesis (TRM). This comprises the inclusion of two or more bases at the codon for a specific amino acid during the synthesis of the oligonucleotide. In doing so, a mutagenic oligonucleotide which can generate all other possible amino acids at a chosen codon can be synthesized. A single amino acid position or a combination of several positions can be mutagenized in that way.

Selective media

Selective media for phenylacetyl L-leucine ('fal') were prepared as described by Garcia (Garcia et al., J. Biotech. 3 (1986) 187–195). Minimal plates are as follows: M63 minimal agar, 2 g/l glucose, 1 mg/l thiamine, 10 mg/l L-proline and the appropriate antibiotic (50 $\mu$g/ml chloramphenicol (cap) or 25 $\mu$g/ml ampicillin (amp)). For selections on side-chain specificity (e.g phenylacetyl, phenoxyacetyl, phenylglycyl, p-hydroxyphenylglycyl, adipyl or $\alpha$-aminoadipyl) of acylases 100 $\mu$g/l of the corresponding acyl L-leucine was included into minimal plates. Transformants or mutants of E. coli HB101 (Leu$^-$) growing exclusively in the presence of the acyl L-leucine are considered to harbour an acylase gene with the desired specificity. Instead of leucine the amino acid moiety of the selective substrate may also be varied. In such case a suitable auxotrophic mutant of E. coli was used for selection. For example, selection on the substrate N-adipyl-L-leucine was carried out with E. coli strain PC2051 as a host (obtained from Phabagen, Utrecht, the Netherlands). The special screenings substrates were purchased from LGSS, Transferbureau Nijmegen, the Netherlands.

Phenylacetyl amide was added to a final concentration of 15 mM to minimal M63 medium supplemented with 0.2% of either succinate, glycerol or glucose as carbon source, and thiamine (1 $\mu$g/ml), L-proline (10 $\mu$g/ml), and the appropriate antibiotic. All salts in the basal medium were replaced by the corresponding salts containing either Na$^+$ or K$^+$ ions in order to ensure selective growth on the amide. Amides with the desired side-chains were purchased from commercial suppliers or prepared according to standard techniques. E. coli strains JM101, WK6, HB101, PC2051 and PC1243 were used as hosts to select for mutant genes with specificity for the selective amides.

Isolation and purification wild type and mutant acylases

Cells were harvested by centrifugation and resuspended in 10 mM sodium phosphate buffer pH 7.4 containing 140 mM NaCl. The cells were disrupted through sonification (6×20 sec, 100 W, 100 mm bar, Labsonic 1510; after every 20 seconds the cells were cooled on ice for 30 seconds). Subsequently, the suspension was centrifugated. The sonification procedure was repeated with the resuspended pellet and finally the cell debris was removed by centrifugation. Via ultra-filtration the supernatant is extensively washed with milli-Q water and subsequently with the starting buffer for the Q-Sepharose: 20 mM NaH$_2$PO$_4$.H$_2$O pH 7.0+azide. Filter system supplied by Filtron with a Verder pump. The cut off of the filter is 5 Kda. After ultra-filtration the sample is diluted with milli-Q until the conductivity is less or equal to the starting buffer.

The sample is applied to a Q-sepharose column equilibrated with 20 mM NaH$_2$PO$_4$.H$_2$O pH 7.0+0.02% azide (conductivity=2.60 mS) and run at a flow of 20 ml/min. The gradient (in 50 min to 100% 20 mM NaH$_2$PO$_4$.H$_2$O+0.5M NaCl pH 7.0+0.02% azide) was started after having washed the column thoroughly with starting buffer. Detection at 280 nm. In a next step the acylase was further purified on Hydroxylapetit (HA-ultragel IBF) equilibrated with 10 mM NaH$_2$PO$_4$.H$_2$O +10 $\mu$M CaCl$_2$+0.02% azide pH 6.8. The column is run at 4 ml/min. The acylase elutes in equilibration buffer. The column is regenerated with 350 mM NaH$_2$PO$_4$.H$_2$O+10 $\mu$M CaCl$_2$+0.02% azide pH 6.8. In case very pure protein is required the first column step (Q-sepharose) is repeated with a longer column.

Protein concentration

The total protein content during isolation and purification was determined using the Bradford method with BSA standard. The protein concentration of pure A. faecalis Penicillin G acylase can be calculated from the molar extinction coefficient at 280 nm. The molar extinction coefficient was calculated using the amino acid composition. The molar extinction coefficient calculated was 161210 M$^{-1}$cm$^{-1}$ which corresponds with an OD of 1.87 for 1 mg/ml at a 1 cm path.

The concentration of catalytic centres of the wild type enzyme was determined by titration of penicillin acylase with Phenyl-methylsulphonylfluoride (PMSF) dissolved in isopropanol at different concentrations. In addition the acylase content of the final acylase samples was determined with analytical reversed phase chromatography. Column: RP300 7 micron 20×2.1 mm. Injection volume 5 $\mu$l. The protein was eluted using a linear gradient starting with 100% A (water) and changing to 80% B (70% acetonitrile in water) in 45 minutes. The acylase is eluted in two peaks corresponding to the $\alpha$ and $\beta$ subunit. Because the acylase content of the samples which was calculated from the active site titration experiments was found to be in line with the acylase content calculated from HPLC data, acylase mutants which did not titrate very well with PMSF were applied to RP-HPLC in order to determine the acylase content.

Penicillin acylase activity was assayed using NIPAB as a substrate.

Enzyme assays

In order to determine enzymatic activity the acylases were incubated with substrate at room temperature in buffered solution. In case $\beta$-lactamase impurity was expected to be present in the enzyme preparations, 1.0 mM $\beta$-lactamase inhibitor 6-bromo-penicillanic acid was added to the assay. The reactions were stopped by adding an excess PMSF. For some mutants which were less sensitive to PMSF inhibition, the reactions were stopped by adding 0.5M HCl or 0.5M acetic acid until the pH was between 3 and 4. When reactions were subsequently analysed by HPLC, the reactions were stopped by dilution with the corresponding elution solvent (see table 1). In addition substrates were incubated under assay conditions in absence of enzyme. If necessary enzyme assays were corrected for non-enzymatic hydrolysis The composition of the reaction mixtures was determined by high-performance liquid chromatography (HPLC)(table 1). Concentrations were determined by using standards of known concentration.

TABLE 1

Procedures for analysis of the composition of enzyme reaction mixtures using high-performance liquid chromatography (HPLC). Reactions were stopped by diluting the reaction mixture with the appropriate solvent which is indicated in the left column. Detection at 214 nm. Flow 1 ml/min. SDS = Sodium dodecylsulphate.

| Sample | Column | Solvent |
|---|---|---|
| PenG 1:1 with solvent A | CP-Microspher C18 (Chrompack, cat.no 28410) | A:30% acetonitrile in 0.1M $KH_2PO_4$ pH 3 with 0.75 g/l SDS |
| PenV 1:1 with solvent A | CP-Microspher C18 | A:30% acetonitrile in 0.1M $KH_2PO_4$ pH 3 with 0.75 g/l SDS |
| CefG 1:1 with solvent A | CP-Microspher C18 | A:20% acetonitrile in 0.05M $KH_2PO_4$ pH 3 wit 0.68 g/l SDS |
| Ampicillin 1:3 with solvent A | CP-Microspher C18 | A:15% acetonitrile in 0.05M $KH_2PO_4$ pH 3 with 0.68 g/l SDS during 6 min; B:A with 50% acetonitrile during 16 min. |
| PGA 1:1 with solvent A | CP-Microspher C18 | A:25% acetonitrile in 0.05M $KH_2PO_4$ pH 3 with 0.68 g/l SDS |
| Amoxicillin 1:2 with solvent A | Chromspher C18 (Chrompack, cat.no 28267) | A:25% acetonitrile in 0.012M $KH_2PO_4$ pH 2.6 with 2 g/l SDS |
| Ampicillin, PGA, PG, 6APA mixtures | Chromspher C18 | A:30% acetonitrile in 0.005M $KH_2PO_4$ pH 3.0 with 0.68 g/l SDS |

At low concentration formation of 6-APA, 7-ACA or 7-ADCA was measured by titration with fluorescamine. Concentrations were determined by measuring the fluorescence at 475 nm after 390 nm excitation. In addition the concentrations of 6-APA, 7-ACA, 7-ADCA were determined using the indicator reaction with p-dimethylaminobenzaldehyde. Formation of a Schiff base was followed at 415 nm (K. Balasingham et al., Biochmica et Biophysica Acta 276 (1972) 250–256).

In a continuous assay Penicillin G acylase was assayed spectrofotometrically with the chromogenic substrate NIPAB [6-nitro-3-phenylacetamido-benzoic acid]. The liberation of 3-amino-6-nitrobenzoic acid was monitored by measuring the extinction at 405 nm in a Kontron 610 kinetic spectrofotometer. Measuring maximal rate, the assays were performed at 25° C. using 20 mM $NaH_2PO_4.H_2O$ at pH 7.5 with 20 mM NIPAB and 100 μl enzyme solution (at a proper dilution). Initial rate measurements were performed with varying concentration of NIPAB.

The kinetics of enzymatic hydrolysis of PenG, PenV, CefG were also studied by alkaline titration (0,01M KOH), using a Radiometer pH-stat. All experiments were carried out in a buffer free medium.

Initial rate measurements were performed with excess substrate over the enzyme. Catalytic parameters were derived from least-squares fitting of the measured initial rates plotted for various substrate concentrations according to the Michaelis-Menten equation.

Deacylation of the acylated L-amino acids which were used in the screening was performed by incubation of the acyl amino acids with enzyme. Subsequently the deacylated amino acids were labeled by a method based on reaction with o-phthaldehyde and mercaptoethanol and quantitated using reversed phase HPLC.

Synthesis reactions were carried out in a pH-stat or in a buffered solution. Typical conditions used: 10 mM PGA, pH 7.0, 30° C. and 30 mM 6-APA. Products were analysed and quantitated by HPLC.

The reaction conditions under which the acylases were tested depend on various parameters, in particular the reagents, reaction time, temperature and enzyme concentration. The preferred conditions can be readily determined by the man skilled in the art. Generally, the reaction temperature may vary between 0° C. and 40° C.

Examples of semi-synthetic β-lactams that may be produced by the application of the mutant acylase of this invention are amoxicillin, ampicillin, cefaclor, cefadroxil, cefprozil, cephalexin, and cephradine.

The acylating agents may be a derivative of D(-)-phenylglycine, D(-)-4-hydroxyphenylglycine or D(-)-2,5-dihydro-phenylglycine such as a lower alkyl (methyl, ethyl, n-propyl or isopropyl) ester or an amide which is unsubstituted in the —$CONH_2$ group.

Generally, the reaction temperature of the process of this invention may vary between 0° C. and 35° C.

EXAMPLES

Example 1

Exploring the Environment of Penicillin G in the Penicillin G-Acylase:PenG Complex and Identification of Residue Position Which Affect the Catalytic Properties of Penicillin G Acylase.

The solvent accessible surface of the *A. faecalis* Penicillin G acylase active site was calculated using the Connolly algorithm. The probe size was 1.4 Å. Contouring of the accessibility using Molecular Graphics revealed a deep hydrophobic cavity near the β-subunit N-terminal serine which was accessible from the solvent. Computer aided docking showed that the phenylacetate fits perfectly in this cavity. After positioning the phenylacetate in the cavity the β-subunit N-terminal serine is in an ideal position for nucleophilic attack at the peptide carbonyl of PenG.

In the subsequent step the β-lactam moiety is positioned while keeping the phenyl-acetyl group fixed in its binding pocket. Atomic overlap between substrate and enzyme is avoided as much as possible while positive interactions are maximized. Relevant positive interactions which contribute to binding are hydrogen bonding, electrostatic interactions and favourable VanderWaals contacts. Hydrophobic interaction was estimated from the accessible non-polar surface which is buried by binding the substrate to the enzyme.

After manual manipulation of the substrate additional computational techniques were applied to optimize the substrate-enzyme complex. Energy minimization and molecular dynamics of the complex were performed using the CVFF forcefield (Biosym Technologies). Minimization was performed in a number of discrete steps. Minimization stopped when first derivative energy less than 0.01 kcal/mol First the complexed PenG substrate was minimized while keeping the acylase atoms fixed. The distance serine B1 OG to PenG scissile carbonyl carbon was constrained between 2 and 3.5 Å. No charges were considered.

Then hydrogen atoms of the acylase were allowed to move.

Subsequently the side chains which have at least one atom within 12 Å of the PenG substrate are allowed to shift while still keeping the backbone fixed. The distance serine B1 OG to PenG scissile carbonyl carbon was still constrained between 2 and 3.5 Å. No charges considered.

After optimization of the side chains also the main chain was allowed to move. First movement was restricted due to tethering the main chain atoms. Gradually the tethering force was relaxed.

Figure 4A:
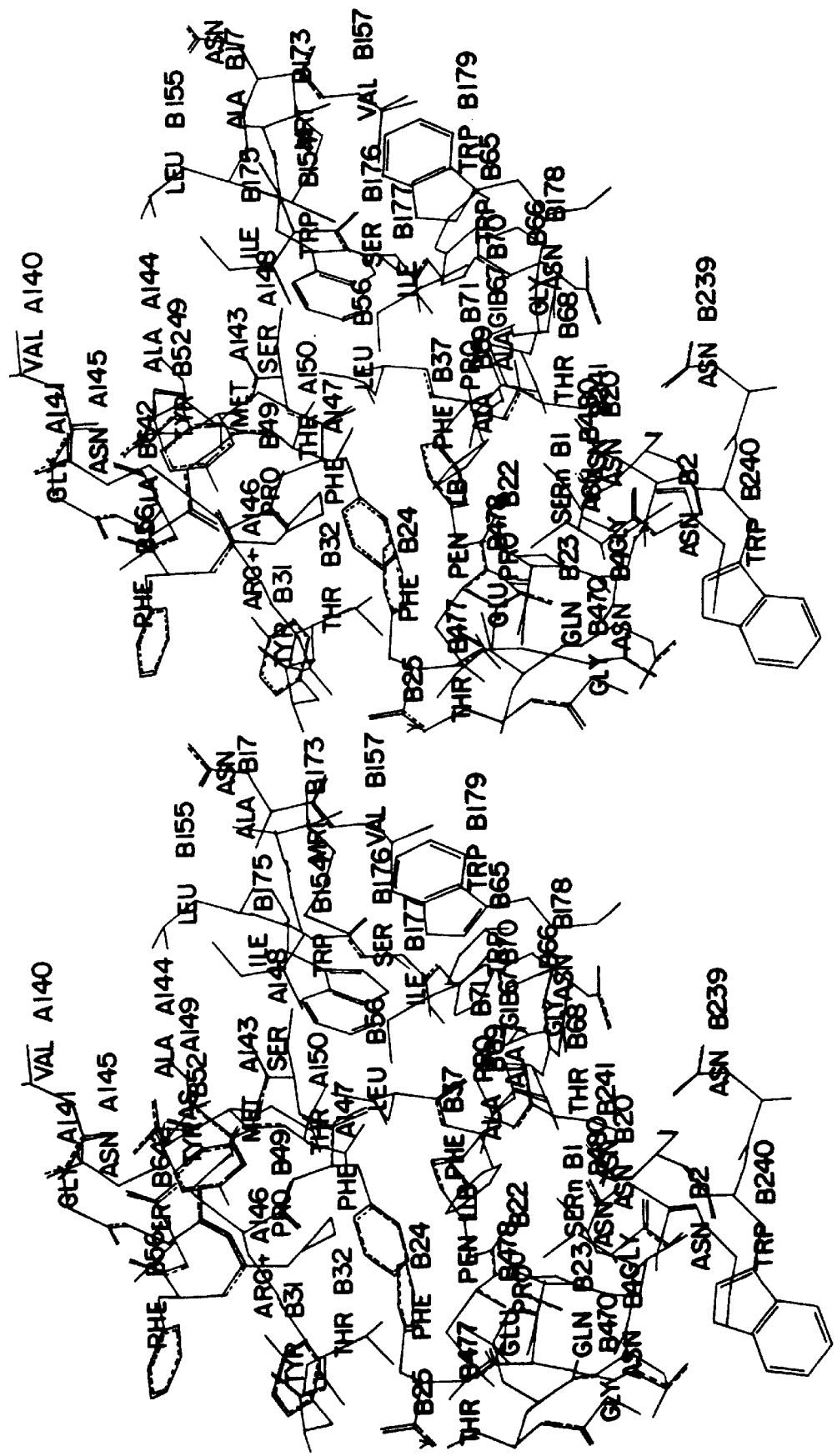
FIG. 4a: Stereo picture of the active site *A. faecalis* PenG acylase around phenylacetyl moiety.

The initial model obtained in this way was used to analyse the environment of the PenG molecule. FIG. 4a shows the residues which form the binding site of the phenylacetate moiety of the PenG substrate. Chain segments involved comprise: A139 to A152 [SEQ ID NO:27], and B1, B2, B20 to B25, B31, B32, B49 to B52, B56, B57, B65 to B72, B154 to B157, B173 to B179, B239 to B241, and B476 to B480 [SEQ ID NO:32]. Table 2 reviews residues which have at least one atom within 8 Å from the PenG phenylacetyl moiety. This survey supplies insight in the residues which interact with the side chain moiety of the penicillin molecule. Essential residues for catalysis should not be replaced as substitution leads to severely crippled or inactive acylases. These residues comprise: B:Ser1, B:Gln23, B:Asn241

Residues in *A. faecalis* Penicillin G acylase which are of particular interest for binding penicillin side chain are: A:Met143, A:Phe147 [SEQ ID NO:27], and B:Pro22, B:Phe24, B:Tyr31, B:Thr32, B:Pro49, B:Tyr52, B:Leu56, B:Phe57, B:Gly66, B:Ala67, B:Thr68, B:Ala69, B:Gly70, B:Pro71, B:Trp154, B:Val157, B:Met173, B:Ile175, B:Ser176, B:Ile177, and B:Trp179 [SEQ ID NO: 32].

Figure 4B:
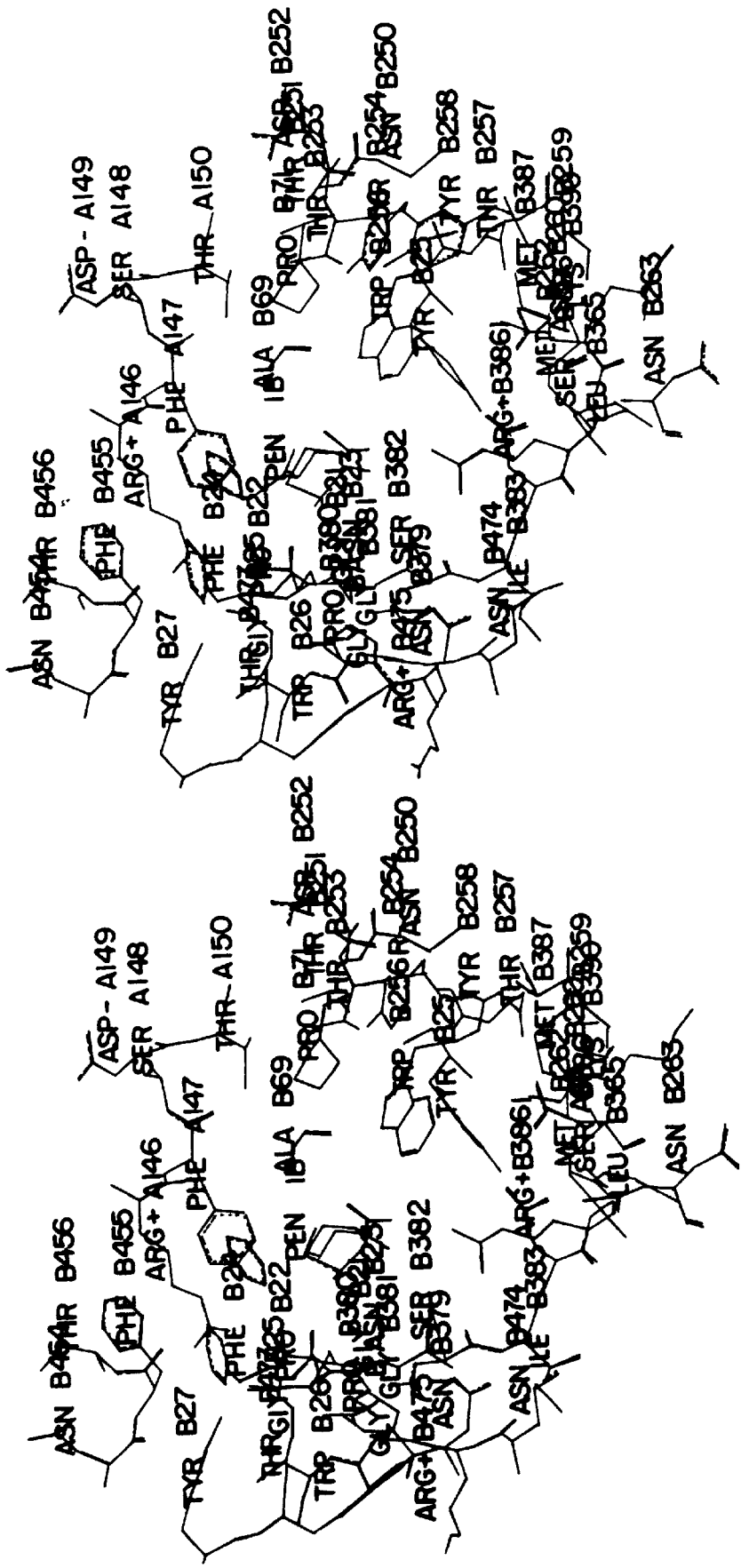
FIG. 4b: Stereo picture of the active site *A. faecalis* PenG acylase around the 6-ACA moiety.

In addition the environment of the β-lactam moiety 6-APA was mapped. Table 3 reviews residues which have at least one atom within 8 Å from an atom in the PenG 6-APA moiety. FIG. 4b shows the residues which form the binding site of the β-lactam moiety of the PenG substrate. Chain segments involved comprise: A146 to A150 [SEQ ID NO:27], and B21 to B27, B71, B250 to B263, B379 to B387, B390, B454 to B456, and B474 to B477 [SEQ ID NO:32]. FIG. 4b shows the *A. faecalis* Penicillin G acylase active site focussing on the residues around the β-lactam moiety Residues in *A. faecalis* Penicillin G acylase which are of particular interest for binding the penicillin β-lactam part are: A:Arg146, A:Phe147, and A:Thr150 [SEQ ID NO:27], and B:Gly25, B:Tyr27, B:Ala69, B:Pro71, B:Thr251, B:Thr253, B:Tyr254, B:Tyr255, B:Trp256, B:Arg261, b:Met262, B:Asn379, B:Pro380, B:Gly381, B:Ser382, B:Ile383, B:Asn384, B:Met387, B:Lys390, B:Thr477, and B:Glu478 [SEQ ID NO: 32].

TABLE 2

Environment of the phenylacetyl moiety in Penicillin G Acylase complexed with PenG Atoms in the acylase with a certain distance range from PenG. Only closest atoms given. Distances in Å. Atom indication: chain-residue nuber:atom

Figure 3:
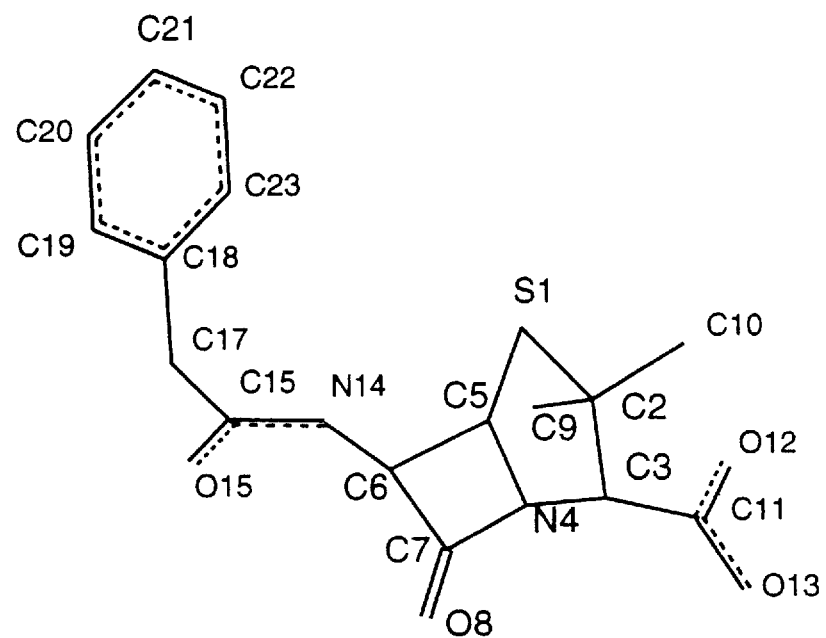
FIG. 3: Atom names PenG referring to nomenclature used in tables 2 and 3.

| PenG atoms (FIG. 3) | 3–4 | 4–5 | 5–6 | 6–7 | 7–8 |
|---|---|---|---|---|---|
| C15 | B1:OG<br>B23:O | A147:CZ<br>B69:CB<br>B241:ND2 | B22:C<br>B24:CD2<br>B68:C | B2:N<br>B21:O<br>B67:O<br>B382:OG | A147:CZ<br>B25:N<br>B70:N<br>B71:CG<br>B240:CD1<br>B256:CZ2<br>B261:CZ<br>B477:OG1 |

TABLE 2-continued

Environment of the phenylacetyl moiety in Penicillin G Acylase complexed with PenG Atoms in the acylase with a certain distance range from PenG. Only closest atoms given. Distances in Å. Atom indication: chain-residue nuber:atom

| PenG atoms (FIG. 3) | 3–4 | 4–5 | 5–6 | 6–7 | 7–8 |
|---|---|---|---|---|---|
| O16 | B1:CB<br>B69:N<br>B241:ND2 | A147:CE2<br>B23:O<br>B68:CA | | B2:N<br>B21:O<br>B22:CA<br>B24:CE2<br>B67:O<br>B70:N<br>B71:CG | B176:O<br>B177:CD1<br>B178:ND2<br>B239:OD1<br>B240:CD1<br>B256:CZ2<br>B261:CZ<br>B382:OG |
| C17 | B1:OG<br>A147:CE2<br>B23:O<br>B24:CD2 | B22:C<br>B69:CB | B68:CA<br>B241:ND2 | A146:CZ<br>B21:O<br>B25:N<br>B57:CZ<br>B67:O | A143:SD<br>B2:N<br>B31:CE2<br>B56:CD2<br>B70:N<br>B177:CD1<br>B477:OG1 |
| C18 | B24:CE2 | A147:CZ<br>B1:CB<br>B22:CB<br>B23:O<br>B68:CA<br>B69:CB | B57:CZ<br>B67:O<br>B241:ND2 | A143:SD<br>B21:O<br>B56:CD2<br>B177:CD1 | A146:CZ<br>B2:N<br>B20:ND2<br>B31:CE2<br>B49:CG<br>B70:N<br>B177:CG1<br>B477:OG1 |
| C19 | A147:CG<br>B24:CE2<br>B69:N | B1:OG<br>B68:C | A143:SD<br>B22:CB<br>B23:O<br>B56:CD2<br>B67:C<br>B177:CD1<br>B241:ND2 | B57:CZ<br>B70:N | A142:O<br>A146:C<br>B31:CE2<br>B49:CG<br>B71:CD<br>B154:CZ2<br>B176:O<br>B175:N |
| C20 | B69:N | A143:SD<br>A147:CB<br>B24:CE2<br>B56:CD2<br>B67:CB<br>B65:C<br>B177:CG2 | B1:OG<br>B22:CB<br>B57:CZ<br>B154:CZ2 | B23:O<br>B49:CG<br>B70:N<br>B176:O<br>B178:N<br>B241:ND2 | A142:O<br>A146:C<br>B20:ND2<br>B31:CE2<br>B52:CE1<br>B66:C<br>B71:CD<br>B173:CE<br>B175:CG2 |
| C21 | B24:CE2<br>B56:CD2 | A143:CE<br>B22:CB<br>B57:CZ<br>B67:CB<br>B68:N<br>B69:N | A147:CD1<br>B1:OG<br>B49:CG<br>B56:CG<br>B154:CZ2<br>B177:CG2 | B20:ND2<br>B23:N<br>B66:C<br>B178:O | B21:C<br>B31:CE2<br>B52:CE1<br>B70:N<br>B176:O<br>B179:CD1<br>B241:ND2 |
| C22 | B22:CB<br>B24:CE2<br>B57:CZ | B1:OG<br>B56:CD2<br>B67:O<br>B68:CA | A143:C<br>A147:C<br>B49:CG | B20:ND2<br>B21:C<br>B23:O<br>B31:CE2<br>B66:C<br>B69:CB<br>B154:CZ2<br>B177:CG2 | B2:O<br>B32:CG2<br>B52:CE1<br>B178:O<br>B41:ND2<br>B478:OE1 |
| C23 | B1:OG<br>B22:CB<br>B24:CD2 | B23:N<br>B57:CZ<br>B67:O<br>B68:CA<br>B69:N | A147:CE1<br>B49:CG<br>B56:CD2 | A143:CE<br>B20:ND2<br>B21:C<br>B31:CE2<br>B241:ND2 | A146:CZ<br>B2:N<br>B32:CG2<br>B56:CB<br>B154:CZ2<br>B177:CG2<br>B478:OE1<br>B477:OG1 |

TABLE 3

Environment of 6-APA moiety in Penicillin G acylase complexed with PenG

Atoms in the acylase within a certain distance range from 6-APA moiety PenG. Only closest atoms given. Distances in Å. Atom indication: chain-residue number:atom

| PenG atoms (FIG. 3) | 3—4 | 4–5 | 5–6 | 6–7 | 7–8 |
|---|---|---|---|---|---|
| S1 | | A147:CE2 | B23:O | A146:NE | B1:OG | B380:C |
| | | | B24:CA | B25:N | B455:CG |
| | | | | B59:CB | |
| | | | | B241:OD1 | |
| | | | | B256:CZ2 | |
| | | | | B381:CA | |
| | | | | B382:N | |
| C2 | | A147:CE2 | B381:CA | A146:NE | B1:N |
| | | B23:O | | B24:N | B69:CB |
| | | | | B25:N | B261:CZ |
| | | | | B241:OD1 | B379:CD1 |
| | | | | B256:NE1 | B383:N |
| | | | | B360:C | B384:ND2 |
| | | | | B382:CA | |
| C3 | | B256:CZ2 | A147:CE2 | B1:N | A146:NE |
| | | B382:OG | B23:O | B241:CG | B24:N |
| | | | B241:OD1 | B261:CZ | B25:N |
| | | | | B381:CA | B69:CB |
| | | | | B384:ND2 | B256:CG |
| | | | | | B379:OD1 |
| | | | | | B380:O |
| | | | | | B383:N |
| N4 | | A147:CE2 | B23:O | B1:N | B24:N |
| | | B241:OD1 | B69:CB | B71:CG | B381:CA |
| | | B256:CZ2 | B382:OG | B261:CZ | |
| | | | | B384:ND2 | |
| C5 | A147:CE2 | B69:CB | B23:O | A146:O | A150:CG2 |
| | | | B241:OD1 | B1:OG | B25:N |
| | | | B256:CZ2 | B24:CA | B261:CZ |
| | | | | B71:CG | B381:CA |
| | | | | B256:CG | |
| | | | | B382:OG | |
| C6 | A147:C1 | B1:OG | B256:CZ2 | B24:N | B2:N |
| | | B23:O | | B68:C | B22:C |
| | | B69:CB | | B71:CG | B70:N |
| | | B241:OD1 | | B261:CZ | B240:C |
| | | | | B382:OGB | B241:N |
| | | | | | B384:ND2 |
| C7 | B241:CD1 | A147:CE2 | B23:O | B71:CG | B2:N |
| | | B1:N | B69:CB | B240:O | B24:N |
| | | B256:CZ2 | B261:CZ | | B68:C |
| | | B382:OG | | | B254:CE1 |
| | | | | | B381:CA |
| | | | | | B384:CG |
| C8 | B1:OD1 | B23:O | A147:CE2 | B69:CB | B2:N |
| | B241:OD1 | B256:CZ2 | B240:NE1 | B241:CA | B22:C |
| | B382:OG | B261:CZ | B384:ND2 | B381:C | B24:N |
| | | | | | B71:CG |
| | | | | | B383:O |
| | | | | | B390:NZ |
| C9 | B23:O | B381:CA | A147:CE2 | A146:CZ | B22:C |
| | N382:N | | B24:CA | B1:OG | B26:CZ3 |
| | | | B25:N | B241:OD1 | B27:OH |
| | | | B380:O | B379:OD1 | B256:CZ2 |
| | | | | B383:N | B261:CZ |
| | | | | | B384:NO2 |
| | | | | | B477:OG1 |
| C10 | | | A147:CE2 | A146:CZ | B256:NE1 |
| | | | B23:O | B24:C | |
| | | | B380:O | B25:N | |
| | | | B381:CA | B379:OD1 | |
| | | | | B380:C | |
| | | | | B381:O | |
| | | | | B382:OG | |
| C11 | | B256:NE1 | B382:OG | A147:CE2 | A150:CG2 |
| | | | | B241:CD1 | B23:O |
| | | | | B384:ND2 | B69:CB |
| | | | | | B71:CG |
| | | | | | B261:CZ |
| | | | | | B381:CA |
| O12 | | B256:NE1 | A147:CE2 | A150:CG2 | A146:O |
| | | | | | B23:O |
| | | | | | B69:CB |
| | | | | | B71:CG |
| | | | | | B241:OD1 |
| | | | | | B382:OG |
| | | | | | B384:ND2 |
| O13 | | B256:NE1 | B382:OG | | A147:CE2 |
| | | | B384:ND2 | | B241:OD2 |
| | | | | | B255:CD1 |
| | | | | | B256:CE3 |
| | | | | | B379:OD1 |
| | | | | | B381:CA |
| | | | | | B383:N |
| | | | | | B384:N |

Example 2

Construction of the Mutagenesis/Expression Vector for Acylase

Figure 5:
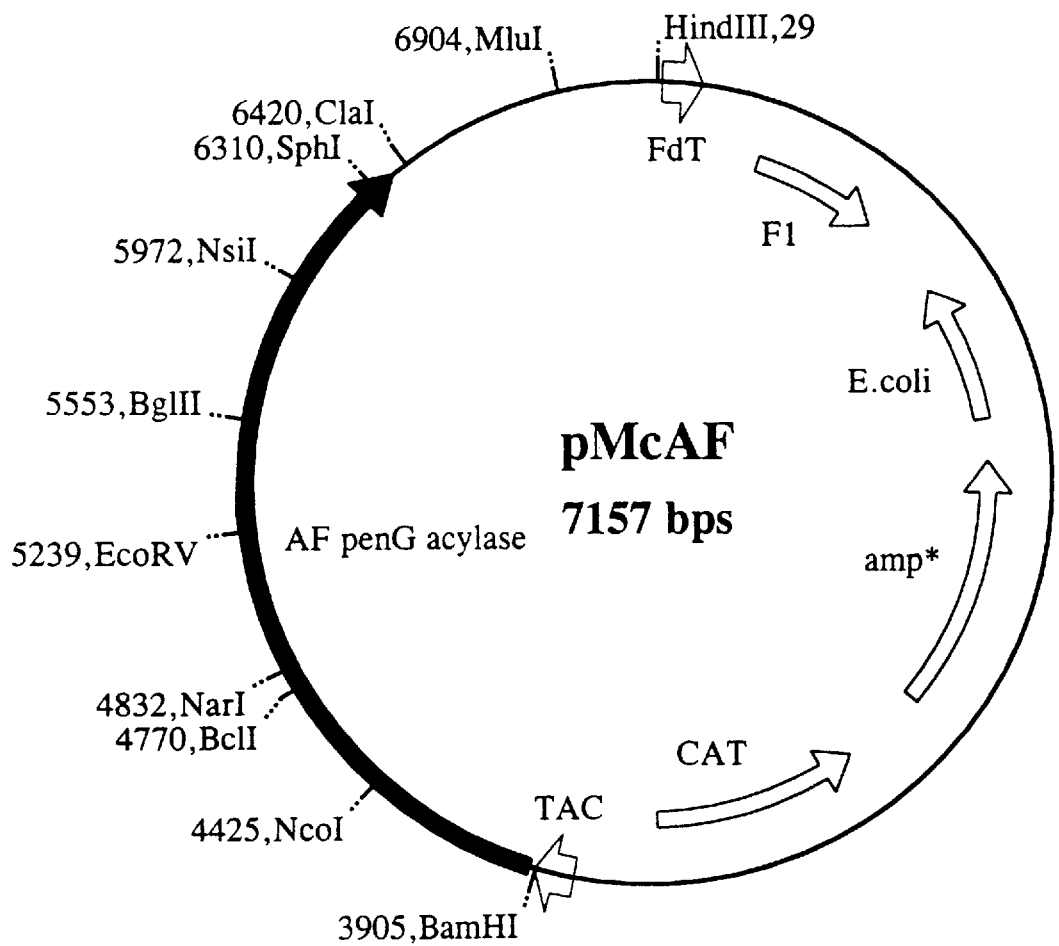
FIG. 5: pMcAF mutagenesis vector with *A. faecalis* Penicillin G acylase gene, *E. coli* ori 'high' copy, Tac promotor, Fd-terminator, cap$^r$, amp$^s$ fl-origin.

As starting material for the construction of a combined mutagenesis/expression vector the already described plasmid pMcTAFNde was used (EP-453048). This vector, which was constructed from pMcTNde and pAF1, harbors the complete penicillin acylase gene from *Alcaligenes faecalis*. In order to facilitate the construction of convenient gapped duplex molecules and to facilitate the exchange of PCR overlap extension fragments three new unique restriction sites were inserted without altering the coding information: EcoRV (position 5239), NsiI (pos. 5972) and ClaI (pos. 6420). The resulting vector, pMcAF, which is shown in FIG. 5, was used to construct mutant acylase genes. The mutant acylases were produced in *E. coli* WK6 or HB101 laqI$^q$ under guidance of the tac promoter provided.

Example 3

Mutagenesis of *A. Faecalis* Acylase

At selected positions amino acid mutations were generated using the PCR overlap extension method described before. The amino acid positions in the respective subunit (A or B) are shown in table 4. The oligonucleotides used for the construction are also shown. Note that at position A143 and B67, B68, B69 an oligo with randomized codons was used.

Example 4

Assay of Site Directed Mutants of Penicillin Acylase for Correct Folding and Post Translational Processing Using Suitable Auxotrophs of *E. Coli*

*E. coli* HB101 laqI$^q$ cells harbouring the identified mutant acylase genes were tested on agar plates containing selective media.

Selective media for phenylacetyl L-leucine ('fal') were prepared as described by Garcia (supra). Minimal plates are as follows: M9 minimal agar, 1 mg/l thiamine, 10 mg/l L-proline, 0.2 mM IPTG and the appropriate antibiotic (50 μg/ml chloramphenicol (cap) or 75 μg/ml ampicillin (amp)). The available data from literature on expression of penicillin acylase indicate that proper folding and posttranslational processing of the chain are critical factors for obtaining catalytical viable penicillin acylase. In order to establish whether the mutant penicillin acylase is expressed properly as an active acylase 200 μg/ml of an acyl L-leucine was included into minimal plates. Transformants or mutants of *E. coli* HB101 (Leu⁻) growing exclusively in the presence of the phenyl-acetyl-L-leucine are considered to harbour an active properly expressed penicillin acylase gene. Table 5 shows the result for several selected mutants.

In addition this method may be employed for an initial rough screening for acylases with an altered specificity. For selections on side-chain specificity of acylases 200 μg/ml of a desired acyl L-leucine was included into minimal plates. In case the acyl moiety is not recognized by the wild type penicillin acylase transformants or mutants of *E. coli* HB101 (Leu⁻) growing exclusively in the presence of the desired acyl L-leucine are considered to harbour an acylase gene with the desired specificity (e.g. glutaryl-L-leucine). Examples of such selective substrates are α-D-aminoadipyl leucine, adipyl-leucine and glutaryl leucine. These compounds were purchased from LGSS, Transferbureau Nijmegen, The Netherlands.

When wild type has low activity for an acyl group, mutants with increased activity can be picked up with this method by comparing the size of the halo produced by the mutant with respect to wild type. Useful side chains are phenoxyacetyl, p-hydroxyphenylglycyl, phenylglycyl.

TABLE 5

In vivo specifity of mutant acylases. A and B in the first column refers to α and β subunit. ++ growth rate comparable to wild type; + growth rate reduce with respect to wild type: − no growth during 3 weeks.

| mutant | fenyl-acetyl-L-leucine |
|---|---|
| A : M143R | + |
| A : M143K | + |
| A : F147Y | ++ |
| A : F147H | ++ |
| A : F147W | ++ |
| B : F24R | − |
| B : F24K | ++ |
| B : L56R | |
| B : L56K | ++ |
| B : L56H | |
| B : I177R | |
| B : I177K | ++ |
| B : I177H | ++ |

Instead of leucine also the amino acid moiety of the selective substrate can be varied. In such case a suitable auxotrophic mutant of *E. coli* was used for selection. Instead also amide of the acyl moiety are useful compounds for selection. Side-chain amide (e.g. phenylacetylamide, glutarylamide, adipylamide, α-D-aminoadipylamide) was added to a final concentration of 15 mM to minimal M9 medium supplemented with 0.2% of either succinate, glyc-

TABLE 4

Synthetic DNA-oligonucleotides for PCR mutation
(X = all possible amino acids)
(R = A or G; Y = C or T; S = C or G; W = A or T; B = C, G or T;
V = A, C, G; N = A, C, G or T)

| A.A.-position | A.A.-mutation | DNA-oligonucleotides: 5'-3' |
|---|---|---|
| A143 | M : R, K | 5' GGGTGGGCTCCARGGCCAATCG 3' [SEQ ID NO:1]. |
| | | 5' GCGATTGGCCYTGGAGCCCAC 3' [SEQ ID NO:2]. |
| A147 | F : Y, H | 5' TGGGCTCCATGGCCAATCGCYACTCCGACACGAA 3' [SEQ ID NO:3]. |
| | F : W | 5' TGGGCTCCATGGCCAATCGCTGGTCCGACACGAA 3' [SEQ ID NO:4]. |
| B24 | F : R, K | 5' CGGCCCACAGARGGGCTGGTACA 3' [SEQ ID NO:5]. |
| | | 5' GTACCAGCCCYTCTGTGGGCC 3' [SEQ ID NO:6]. |
| B56 | L : R, K | 5' TCCGATCGTAARGTTTGGCACC 3' [SEQ ID NO:7]. |
| | | 5' GGTGCCAAACYTTACGATCGGAT 3' [SEQ ID NO:8]. |
| | L : H | 5' TCCGATCGTACATTTTGGCACC 3' [SEQ ID NO:9]. |
| | | 5' GGTGCCAAAATGTACGATCGGAT 3' [SEQ ID NO:10]. |
| | L : G, A, V | 5' CCGATCGTAGBCTTTGGCAC 3' [SEQ ID NO:11]. |
| | | 5' GTGCCAAAGVCTACGATCGG 3' [SEQ ID NO:12]. |
| B71 | P : F, Y | 5' GCTGGCTWCCAAGATGTGGTG 3' [SEQ ID NO:13]. |
| | | 5' ATCTTGGWAGCCAGCAGTCGC 3' [SEQ ID NO:14]. |
| B177 | I : R, K | 5' GATGGCGATATCCARGAACTGGTACTA 3' [SEQ ID NO:15]. |
| | I : H | 5' GATGGCGATATCCCACAACTGGTACTA 3' [SEQ ID NO:16]. |
| | I : V, M | 5' CAGCAAGATGGCGATATCCRTGAACTGGTACTACGC 3' [SEQ ID NO:17]. |
| | I : S, T | 5' CAGCAAGATGGCGATATCCASCAACTGGTACTACGC 3' [SEQ ID NO:18]. |
| A143 | M : X | 5' GGGTGGGCTCCNNSGCCAATCGCTTCTC 3' [SEQ ID NO:19]. |
| | | 5' AAGCGATTGGCSNNGGAGCCCACCCAG 3' [SEQ ID NO:20]. |
| B67 | A : S, G, T | 5' GGGR/SCACTGCTGGGCCTCAAG 3' [SEQ ID NO:21]. |
| | | 5' AGTGSIYCCCCCAGGCAATCTC 3' [SEQ ID NO:22]. |
| | A : S, G | 5' GCCTGGGGGRCACTGCTGGCCCGCAAG 3' [SEQ ID NO:23]. |
| | | 5' GCCAGCAGTGCYCCCCCAGGCAATCTC 3' [SEQ ID NO:24]. |
| B67 | A : X | 5' CGAGATTGCCTGGGGGNNSNNSNNSGGCCCGCAAGATGTGGTGGAC 3' [SEQ ID NO:25]. |
| B68 | T : X | 5' CCACATCTTGCGGGCCSNNSNNSNNCCCCCAGGCAATCTCGC 3' [SEQ ID NO:26]. |
| B69 | A : X | | erol or glucose as carbon source, and thiamine (1 µg/ml), L-proline (10 µg/ml), 0.2 mM IPTG and the appropriate antibiotic.

All ammonium salts in the basal medium were replaced by the corresponding salts containing either Na+ or K+ ions in order to ensure selective growth on the amide. Amides with the desired side-chains were purchased from commercial suppliers or prepared according to standard techniques. *E. coli* strains JM101, WK6 and HB101 were used as hosts to select for mutant genes with specificity for the selective amides.

Example 5

Assay on Targeted Random Mutants of Penicillin Acylase

In case of TRM mutagenesis a pool of mutants was plated on selective plates prior to DNA sequencing. Only the colonies which showed growth on one ore more of the selective media were characterized. The result for 2 TRM mutagenesis experiments are shown in table 6.

TABLE 6

In vivo specificity of mutant acylases. A in the first colunn refers to the α subunit. ++ growth rate comparable to wild type; + growth rate reduce with respect to wild type; − no growth during 3 weeks.

| mutant | fenyl-acetyl-1-leucine |
|---|---|
| A : M143C | ++ |
| A : M143G | + |
| A : M143D | + |
| A : M143T | ++ |
| A : M143V | ++ |
| A : M143L | ++ |

Example 6

Increased Specific Activity and Altered Specificity

The catalytic parameters of *A.faecalis* PenG acylase mutants were determined for different substrates. The altered specificities for the mutants are exemplified in Tables 7 and 8. Compared to wild type the mutants A:M143V and B:L56K exhibit a higher turn-over rate for the deacylation of PenV and CefG. A:F147Y is more active compared to wild type when used in the deamidation of D-phenylglycinamide.

Figure 6:
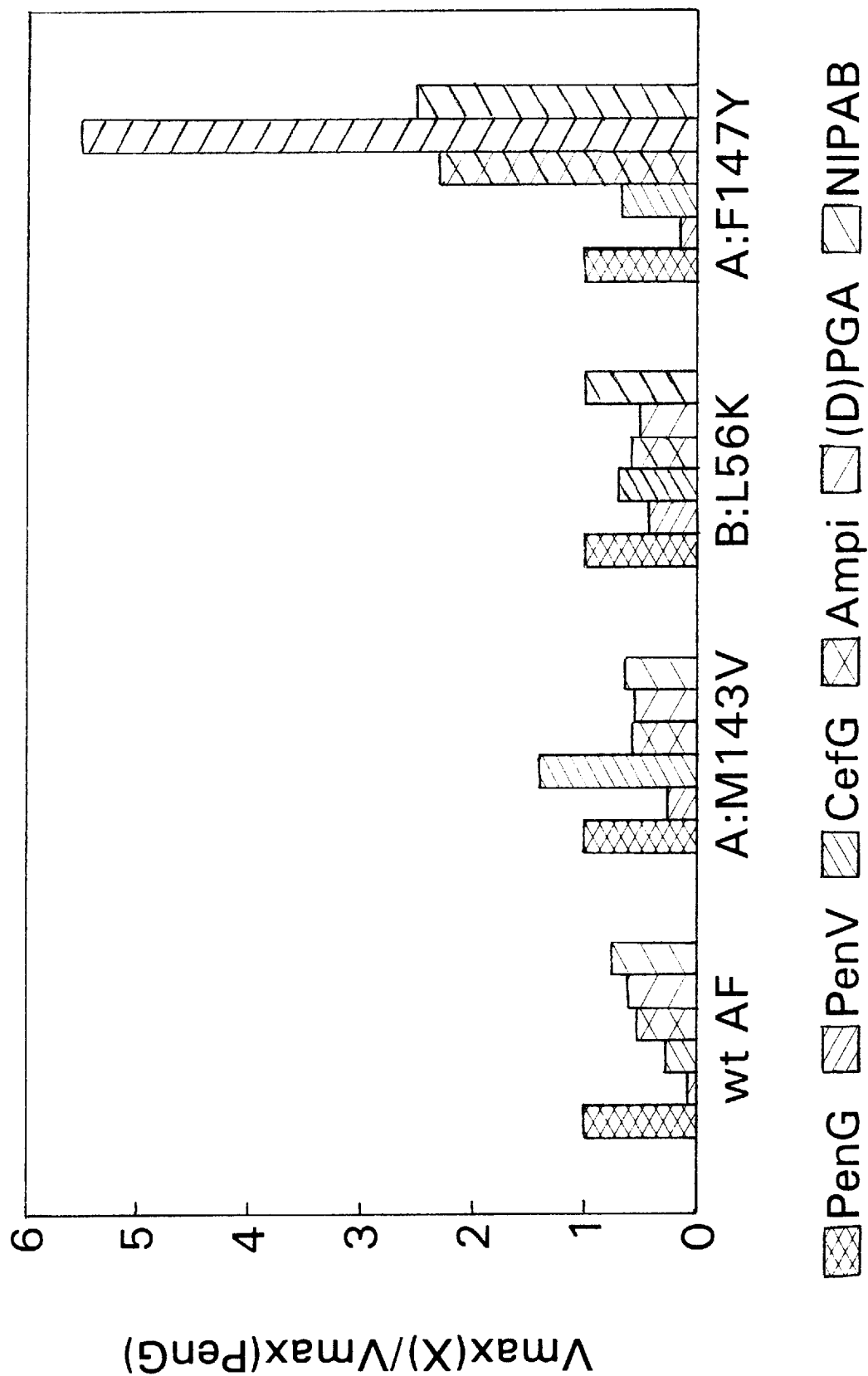
FIG. 6: Maximal deacylation velocity of wild type *A. faecalis* acylase and the mutants B:L56G, B:L56A, B:L56V, B:I177V, B:I177S, B:A67S, B:A67G for various substrates. Velocities for each variant are relative to PenG: $V_{max}(X)/V_{max}(PenG)$. X represents PenV, CefG, Ampicillin (Ampi), (D)Phenylglycinamide ((D)PGA) or NIPAB.
Figure 7:
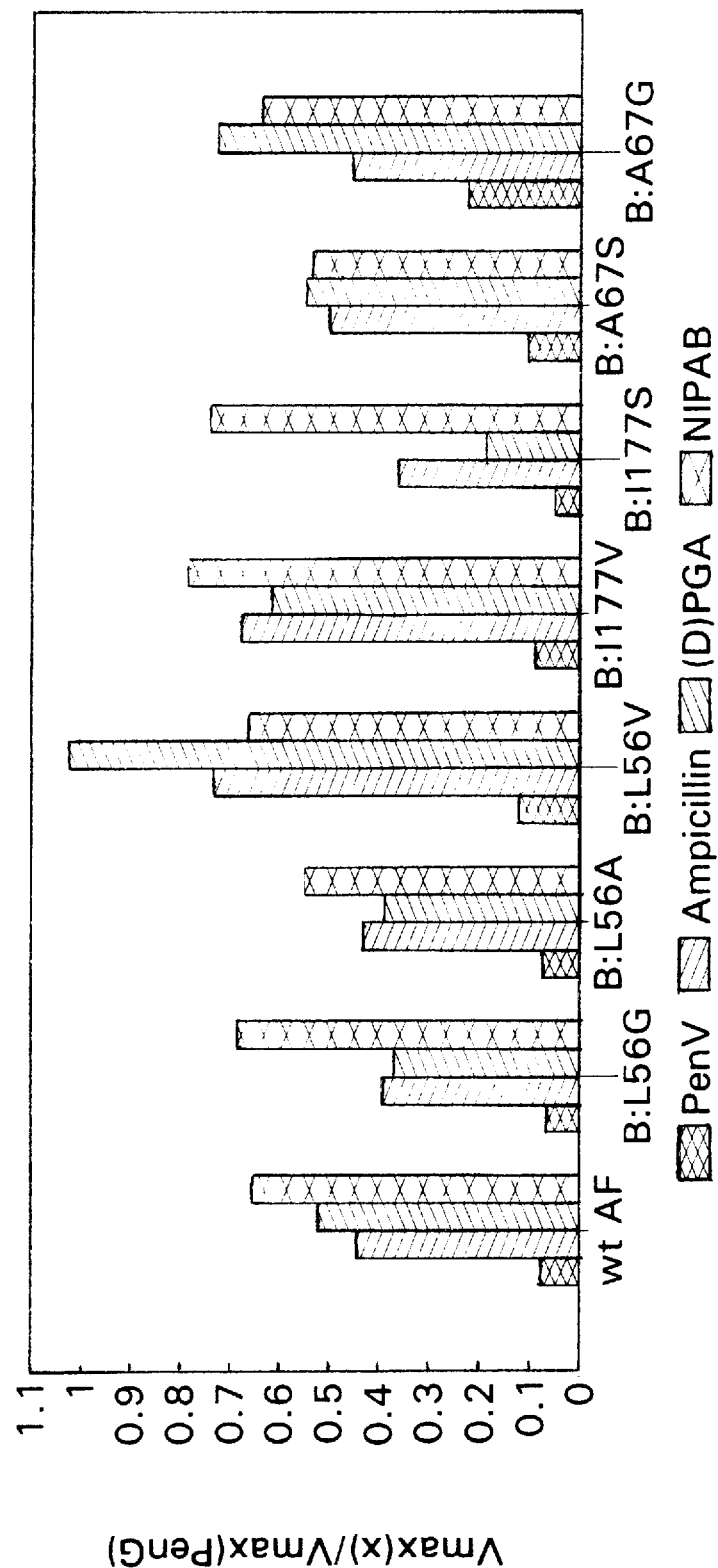
FIG. 7: The maximal deacylation velocity of wild type *A. faecalis* acylase and the mutants A:M143V, B:L56K, A:F147Y for various substrates. Velocities for each variant are relative to PenG: $V_{max}(X)/V_{max}(PenG)$. X represents PenV, CefG, Ampicillin (Ampi), (D)Phenylglycinamide ((D)PGA) or NIPAB.

At high substrate concentrations, which is usually the situation in many industrial conversion processes, the acylase will be completely saturated with substrate and as a consequence the conversion will proceed at maximal velocity. In FIG. 6 the maximal velocity for a number of substrates is plotted for the wild type *A. faecalis* acylase and for some mutants. Velocities are scaled relative to PenG whereby $V_{max}$ for PenG has been set to 1. Wild type PenG acylase shows the highest activity for PenG as was expected. However the substitution A:M143V turns the enzyme into a CefG acylase, while the substitution A:F147Y turns the enzyme into a powerful amidase for the deamidation of D-Phenylglycinamide ((D)PGA). In addition the deacylation velocities of A:F147Y are higher for ampicillin and NIPAB than for PenG. In FIG. 7 the $V_{max}$ value which was measured for mutants B:L56G, B:L56A, B:L56V, B:I77V, BI177S, B:A67S, B:A67G for the given substrates is compared to the $V_{max}$ for PenG in a similar way as was done in FIG. 6. Specificity has shifted with respect to wild type. E.g. mutant B:I177S exhibits a reduced deacylation rate on ampicillin and an improved activity on D-phenylglycinamide ((D)PGA).

In general the specificity or selectivity of an enzyme in the sense of discrimination between two competing substrates is determined by comparing the ratio $V_{max}/K_m$ (or $k_{cat}/K_m$) of the two substrates. In table 9 this ratio has been compared for different substrate combinations. Especially the considerable increase of the specificity of the A:F147Y mutant for (D)PGA is striking.

TABLE 9

Selectivity of the wild type enzyme compared to the selectivity of the mutants for a number of substrates.

$(V_{sax}/K_s)_{S1}/(V_{sax}/K_s)_{S2}$
$(\times 100)$

| S1 | S2 | wide type | A:M143V | B:L56K | A:F147Y |
|---|---|---|---|---|---|
| PenV | PenG | 0.97 | 4.93 | 1.21 | 1.10 |
| CefG | PenG | 54.95 | 119.33 | 7.00 | 44.44 |
| PenV | CefG | 1.76 | 4.13 | 17.35 | 2.48 |
| Ampi | PenG | 14.80 | 22.70 | 3.40 | 35.30 |
| (D) PGA | Ampi | 9.50 | 4.10 | 3.00 | 367.60 |

TABLE 7

Catalytic parameters $K_s$ and $V_{sax}$ as were determined for wild type *Alcaligenes faecalis* PenG acylase and some mutants. Assay conditions: NIPAB, 0.1M NaH2PO$_4$, pH 7.5, 25° C.; PenG and PenV, 40 mM NaH$_2$PO$_4$, pH 7.5, 37° C.; CefG, 20 mM NaH$_2$PO$_4$, pH 7.5, 37° C.; Amoxi (cillin), Ampi (cillin) and D-Phenylglycineamide ((D) PGA), 20 mM NaH$_2$PO$_4$, pH 7.0, 37° C.

| | wild type | | A:M143V | | B:L56K | | A:F147Y | |
|---|---|---|---|---|---|---|---|---|
| | $K_s$ (µM) | $V_{sax}$ (U/mg) | $K_s$ (µM) | $V_{sax}$ (U/mg) | $K_s$ (µM) | $V_{sax}$ (U/mg) | $K_s$ (µM) | $V_{sax}$ (U/mg) |
| NIPAB | 4 | 37.0 | 17 | 35.7 | 28 | 47.3 | 5 | 18.0 |
| PenG | 2 | 45.5 | 6 | 40.5 | 1 | 36.4 | 4 | 5.9 |
| PenV | 18 | 4.0 | 31 | 10.3 | 35 | 15.5 | 51 | 0.8 |
| CefG | 1 | 12.5 | 7 | 56.4 | 10 | 25.5 | 6 | 4.0 |
| Ampi | 700 | 23.5 | 1500 | 23.0 | 1700 | 20.9 | 2600 | 13.6 |
| (D) PGA | 8600 | 27.5 | 35000 | 22.2 | 49000 | 18.2 | 1700 | 32.7 |
| Amoxi | 14000 | .9 | 21000 | .2 | | | 19000 | 0.1 |

TABLE 8

Catalytic parameters $K_s$ and $V_{sax}$ as were determined for wild type *Alcaligenes faecalis* PenG acylase and some mutants. Assay conditions: NIPAB, 0.1M NaH2PO4, pH 7.5, 25° C. For mutants B:A67S and B:A67G $V_{sax}$ in U/ml.

| | $K_s$ (μM) | $V_{sax}$ (U/mg) | $V_{sax}/K_s$ |
|---|---|---|---|
| wt AF | 4 | 37.0 | 9.3 |
| B: L56G | 12 | 21.3 | 1.8 |
| B: L56A | 14 | 37.1 | 2.7 |
| B: L56V | 9 | 28.2 | 3.1 |
| B: I177V | 10 | 34.5 | 3.5 |
| B: I177S | 76 | 30.2 | 0.4 |
| B: A67S | 5 | 7.1 | |
| B: A67G | 11 | 1.1 | |

Example 7

Improved Stereospecificity of PenG Acylase

Wild type *A.faecalis* and *E. coli* PenG acylase show a preference for the D enantiomer of penicillins with an α-carbon substituted side chain. Examples are ampicillin, cefalexin, amoxicillin, cefadroxyl, and cefaclor. An increased stereospecifity of Penicillin G acylases is desired in order to obtain Penicillin G acylase which shows an improved enantiomeric excess in conversions with racemic mixtures of chiral compounds. Such property makes the Penicillin G acylase extremely useful for synthesis of enantiomerically pure semisynthetic antibiotics from racemic mixtures of α-carbon substituted phenylacetyl side chains or activated derivatives of the α-carbon substituted phenylacetyl side chain (e.g. phenylglycine-amides or -esters, p-hydroxyphenylglycine-amides or -esters) which contain a chiral α-carbon due to the presence of an amino group (e.g. Ampicillin, Cefalexin, Amoxycillin, Cefadroxyl, Cephachlor) or a hydroxyl group (Cephamandol).

Table 10 shows that for phenylglycinamide wild type PenG acylases show a preference for the D enantiomer. For a racemic mixture (1:1) of D and L phenylglycineamide $v_D/v_L$ equals $(v_{max}/K_m)^{D-PGA}/(v_{max}/K_m)^{L-PGA}$ where $v_D$ and $v_L$ represent velocities of deamidation of D and L enantiomer respectively. So for the wild type *A.faecalis* the velocity of deamidation of the D enantiomer is 5 times faster than for the L enantiomer. For mutant A:F143Y the steroselectivity which is expressed as $(V_{max}/K_m)^{D-PGA}/(V_{max}/K_m)^{L-PGA}$ has increased from 5.10 to 36.52. This means that the velocity of deamidation of D enantiomer is 36.52 times faster than that of L instead of only 5.10 times as for the wild type.

TABLE 10

Stereospecificity of the wild type enzymes *A. faecalis* and *E. coli* versus stereospecificity of the mutants for DL-phenylglycinamide (PGA). Assay conditions DL phenylglycineanide (PGA): 20 mM NaH2PO4, pH 7.0, 37° C.

| | $(V_{sax}/K_2)^{D-PGA}/(V_{sax}/K_2)^{L-PGA}$ |
|---|---|
| Wild type *E. coli* | 3.32 |
| Wild type *A. faecalis* | 5.10 |
| A: M143V | 5.70 |
| B: L56K | 3.25 |
| A: F147Y | 36.52 |

Example 8

Reduced Product Inhibition.

The complete conversion of NIPAB was followed as a function of time at 20, 50 and 100 μM NIPAB by following the increase in absorbtion at 405 nm. Products of this conversion are phenylacetic acid and 3-amino-6-nitrobenzoic acid. The conversion was performed at 25° C. in 0.1M NaH$_2$PO$_4$.H$_2$O buffer pH 7.5. The progress curves of the deacylation of NIPAB could be fitted very well when product inhibition by phenylacetic acid was taken into account. The dissociation constants (usually referred to as inhibition constant $K_i$) for phenylacetic acid which could be derived from the progress curves is shown in table 11. The benefits of some mutants which are less sensitive to product inhibition are shown in table 12. For these mutants the yield of the conversion in a fixed time span is higher than for wild type. Alternatively, in order to obtain a certain yield a shorter conversion time is needed for the mutants.

The conversion of PenG is usually performed at concentrations as high as 200 mM. Using an identical amount of PenG units, the mutant A:M143V may reach in 20 minutes a conversion yield of 90% while wild type approaches 84% in this time span.

TABLE 11

Inhibition of PenG acylase by phenylacetic acid(PA). $K_i$ (inhibition constant PA) represents the dissociation constant. The catalytic parameters vere determined at 25° C. in 0.1M NaH$_2$PO$_4$.H$_2$O buffer pH 7.5.

| | $K_i^{Phenylacetic\ acid}$ (μM) |
|---|---|
| wt AF | 11 |
| B: L56K | 115 |
| B: L56V | 31 |
| B: L56A | 59 |
| B: L56G | 55 |
| B: A67G | 65 |
| B: I177S | 252 |
| B: I177V | 35 |
| A: M143V | 74 |

TABLE 12

Progress of the NIPAB conversion in time. The yield represents the fraction of substrate which has been converted. Conversion of 200 μM NIPAB, 25° C. in 0.1M NaH$_2$PO$_4$.H$_2$O buffer pH 7.5 using 0.1 Unit of enzyme (NIPAB units).

| | Yield (%) 15 min | Yield (%) 30 min |
|---|---|---|
| wt AF | 61.8 | 91.8 |
| B: L56A | 61.3 | 93.3 |
| B: L56G | 62.3 | 94.5 |
| B: A67G | 63.8 | 96.4 |
| A: M143V | 60.5 | 92.7 |

Example 9

Altered Molar Ratio Aminolysis/Hydrolysis. The Synthesis of Ampicillin from (D)phenylglycinamide (D-PGA) and 6APA Using PenG Acylases.

To a buffered solution containing (D)phenylglycinamide (D-PGA) and 6APA PenG acylase wild type or mutants were added. At different time intervals samples were analyzed and the composition of the samples was determined according to the methods described in the experimental section. The results are shown in tables 13 and 14. Some mutants show improved molar ratio aminolysis/hydrolysis.

TABLE 13

Molar ratio aminolysis or synthesis versus hydrolysis (S/H) obtained in the synthesis of ampicillin by PenG acylases. Initial concentrations 12.4 mM D-PGA and 62 mM ampicillin. Experimental conditions: 0.1M Tris buffer pH 7.8, temperature 4° C., enzymes dosed at 0.7 NIPAB units per ml.

| | Aminolysis/Hydrolysis molar ratio: Ampicillin/D-Phenylglycine | | | |
|---|---|---|---|---|
| | t = 5 min | t = 15 min | t = 30 min | t = 60 min |
| wt AF | 0.95 | 0.92 | 0.69 | 0.36 |
| A: M143V | 0.75 | 0.92 | 0.94 | 0.71 |
| B: L56G | 0.78 | 1.03 | 1.02 | 0.79 |
| B: I177S | 0.30 | 0.79 | 1.05 | 1.17 |

TABLE 14

Molar ratio aminolysis or synthesis over hydrolysis (S/H) obtained in the synthesis of ampicillin by PenG acylases. Initial concentrations 10 mM D-PGA and 30 mM ampicillin. Exprimental conditions: 0.1M Tris buffer pE 7.8, temperature 25° C., enzymes dosed at 1.4 D-PGA units per ml.

| | Aminolysis/Hydrolysis molar ratio: Ampicillin/D-Phenylglycine | | |
|---|---|---|---|
| | t = 10 min | t = 30 min | t = 60 min |
| wt AF | 0.43 | 0.20 | 0.06 |
| A: M143V | 0.50 | 0.31 | 0.15 |

SEQUENCE LISTING ( 1 ) GENERAL INFORMATION:

( i i i ) NUMBER OF SEQUENCES: 36

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:1:

G G G T G G G C T C    C A R G G C C A A T    C G            2 2

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:2:

G C G A T T G G C C    Y T G G A G C C C A    C            2 1

( 2 ) INFORMATION FOR SEQ ID NO:3:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:3:

TGGGCTCCAT GGCCAATCGC YACTCCGACA CGAA 34

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:4:

TGGGCTCCAT GGCCAATCGC TGGTCCGACA CGAA 34

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:5:

CGGCCCACAG ARGGGCTGGT ACA 23

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:6:

GTACCAGCCC YTCTGTGGGC C 21

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:7:

TCCGATCGTA ARGTTTGGCA CC 22

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:8:

GGTGCCAAAC YTTACGATCG GAT 23

(2) INFORMATION FOR SEQ ID NO:9:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:9:

TCCGATCGTA CATTTTGGCA CC 22

( 2 ) INFORMATION FOR SEQ ID NO:10:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:10:

GGTGCCAAAA TGTACGATCG GAT 23

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:11:

CCGATCGTAG BCTTTGGCAC 20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:12:

GTGCCAAAGV CTACGATCGG 20

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:13:

GCTGGCTWCC AAGATGTGGT G 21

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:14:

ATCTTGGWAG CCAGCAGTCG C 21

( 2 ) INFORMATION FOR SEQ ID NO:15:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:15:

GATGGCGATA TCCARGAACT GGTACTA 27

( 2 ) INFORMATION FOR SEQ ID NO:16:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:16:

GATGGCGATA TCCCACAACT GGTACTA 27

( 2 ) INFORMATION FOR SEQ ID NO:17:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:17:

CAGCAAGATG GCGATATCCR TGAACTGGTA CTACGC 36

( 2 ) INFORMATION FOR SEQ ID NO:18:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:18:

CAGCAAGATG GCGATATCCA SCAACTGGTA CTACGC 36

( 2 ) INFORMATION FOR SEQ ID NO:19:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:19:

GGGTGGGCTC CNNSGCCAAT CGCTTCTC                                              28

( 2 ) INFORMATION FOR SEQ ID NO:20:

( i ) SEQUENCE CHARACTERISTICS:
          ( A ) LENGTH: 27 base pairs
          ( B ) TYPE: nucleic acid
          ( C ) STRANDEDNESS: single
          ( D ) TOPOLOGY: linear ( i i ) MOLECULE TYPE: other nucleic acid ( x i ) SEQUENCE DESCRIPTION: SEQ ID NO:20:

AAGCGATTGG CSNNGGAGCC CACCCAG                                               27

( 2 ) INFORMATION FOR SEQ ID NO:21:

( i ) SEQUENCE CHARACTERISTICS:
          ( A ) LENGTH: 21 base pairs
          ( B ) TYPE: nucleic acid
          ( C ) STRANDEDNESS: single
          ( D ) TOPOLOGY: linear ( i i ) MOLECULE TYPE: other nucleic acid ( x i ) SEQUENCE DESCRIPTION: SEQ ID NO:21:

GGGVCACTGC TGGGCCTCAA G                                                     21

( 2 ) INFORMATION FOR SEQ ID NO:22:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: other nucleic acid ( x i ) SEQUENCE DESCRIPTION: SEQ ID NO:22:

AGTGBCCCCC AGGCAATCTC                                                       20

( 2 ) INFORMATION FOR SEQ ID NO:23:

( i ) SEQUENCE CHARACTERISTICS:
          ( A ) LENGTH: 27 base pairs
          ( B ) TYPE: nucleic acid
          ( C ) STRANDEDNESS: single
          ( D ) TOPOLOGY: linear ( i i ) MOLECULE TYPE: other nucleic acid ( x i ) SEQUENCE DESCRIPTION: SEQ ID NO:23:

GCCTGGGGGR CACTGCTGGC CCGCAAG                                               27

( 2 ) INFORMATION FOR SEQ ID NO:24:

( i ) SEQUENCE CHARACTERISTICS:
          ( A ) LENGTH: 27 base pairs
          ( B ) TYPE: nucleic acid
          ( C ) STRANDEDNESS: single
          ( D ) TOPOLOGY: linear ( i i ) MOLECULE TYPE: other nucleic acid ( x i ) SEQUENCE DESCRIPTION: SEQ ID NO:24:

GCCAGCAGTG CYCCCCCAGG CAATCTC                                               27

( 2 ) INFORMATION FOR SEQ ID NO:25:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:25:

CGAGATTGCC TGGGGGNNSN NSNNSGGCCC GCAAGATGTG GTGGAC     46

( 2 ) INFORMATION FOR SEQ ID NO:26:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: other nucleic acid ( x i ) SEQUENCE DESCRIPTION: SEQ ID NO:26:

CCACATCTTG CGGGCCSNNS NNSNNCCCCC AGGCAATCTC GC     42

( 2 ) INFORMATION FOR SEQ ID NO:27:

( i ) SEQUENCE CHARACTERISTICS:
    ( A ) LENGTH: 202 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:27:

```
Gln  Val  Gln  Ser  Val  Glu  Val  Met  Arg  Asp  Ser  Tyr  Gly  Val  Pro  His
 1              5                  10                  15
Val  Phe  Ala  Asp  Ser  His  Tyr  Gly  Leu  Tyr  Tyr  Gly  Tyr  Gly  Tyr  Ala
              20                  25                  30
Val  Ala  Gln  Asp  Arg  Leu  Phe  Gln  Met  Asp  Met  Ala  Arg  Arg  Ser  Phe
         35                  40                  45
Val  Gly  Thr  Thr  Ala  Ala  Val  Leu  Gly  Pro  Gly  Glu  Gln  Asp  Ala  Tyr
     50                  55                  60
Val  Lys  Tyr  Asp  Met  Gln  Val  Arg  Gln  Asn  Phe  Thr  Pro  Ala  Ser  Ile
65                  70                  75                  80
Gln  Arg  Gln  Ile  Ala  Ala  Leu  Ser  Lys  Asp  Glu  Arg  Asp  Ile  Phe  Arg
                 85                  90                  95
Gly  Tyr  Ala  Asp  Gly  Tyr  Asn  Ala  Tyr  Leu  Glu  Gln  Val  Arg  Arg  Arg
            100                 105                 110
Pro  Glu  Leu  Leu  Pro  Lys  Glu  Tyr  Val  Asp  Phe  Asp  Phe  Gln  Pro  Glu
       115                 120                 125
Pro  Leu  Thr  Asp  Phe  Asp  Val  Val  Met  Ile  Trp  Val  Gly  Ser  Met  Ala
     130                 135                 140
Asn  Arg  Phe  Ser  Asp  Thr  Asn  Leu  Glu  Val  Thr  Ala  Leu  Ala  Met  Arg
145                 150                 155                 160
Gln  Ser  Leu  Glu  Lys  Gln  His  Gly  Pro  Glu  Arg  Gly  Arg  Ala  Leu  Phe
                165                 170                 175
Asp  Glu  Leu  Leu  Trp  Ile  Asn  Asp  Thr  Thr  Ala  Pro  Thr  Thr  Val  Pro
            180                 185                 190
Ala  Pro  Ala  Ala  Glu  His  Lys  Pro  Gln  Ala
       195                 200
```

(2) INFORMATION FOR SEQ ID NO:28:

(i) SEQUENCE CHARACTERISTICS:
    (A) LENGTH: 209 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:28:

```
Glu Gln Ser Ser Ser Glu Ile Lys Ile Val Arg Asp Glu Tyr Gly Met
 1               5                  10                  15
Pro His Ile Tyr Ala Asn Asp Thr Trp His Leu Phe Tyr Gly Tyr Gly
             20                  25                  30
Tyr Val Val Ala Gln Asp Arg Leu Phe Gln Met Glu Met Ala Arg Arg
         35                  40                  45
Ser Thr Gln Gly Thr Val Ala Glu Val Leu Gly Lys Asp Phe Val Lys
     50                  55                  60
Phe Asp Lys Asp Ile Arg Arg Asn Tyr Trp Pro Asp Ala Ile Arg Ala
65                  70                  75                  80
Gln Ile Ala Ala Leu Ser Pro Glu Asp Met Ser Ile Leu Gln Gly Tyr
                 85                  90                  95
Ala Asp Gly Met Asn Ala Trp Ile Asp Lys Val Asn Thr Asn Pro Glu
             100                 105                 110
Thr Leu Leu Pro Lys Gln Phe Asn Thr Phe Gly Phe Thr Pro Lys Arg
             115                 120                 125
Trp Glu Pro Phe Asp Val Ala Met Ile Phe Val Gly Thr Met Ala Asn
     130                 135                 140
Arg Phe Ser Asp Ser Thr Ser Glu Ile Asp Asn Leu Ala Leu Leu Thr
145                 150                 155                 160
Ala Leu Lys Asp Lys Tyr Gly Val Ser Gln Gly Met Ala Val Phe Asn
                 165                 170                 175
Gln Leu Lys Trp Leu Val Asn Pro Ser Ala Pro Thr Thr Ile Ala Val
             180                 185                 190
Gln Glu Ser Asn Tyr Pro Leu Lys Phe Asn Gln Gln Asn Ser Gln Thr
             195                 200                 205
Ala
```

(2) INFORMATION FOR SEQ ID NO:29:

(i) SEQUENCE CHARACTERISTICS:
    (A) LENGTH: 209 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:29:

```
Ala Ser Pro Pro Thr Glu Val Lys Ile Val Arg Asp Glu Tyr Gly Met
 1               5                  10                  15
Pro His Ile Tyr Ala Asp Asp Thr Tyr Arg Leu Phe Tyr Gly Tyr Gly
             20                  25                  30
Tyr Val Val Ala Gln Asp Arg Leu Phe Gln Met Glu Met Ala Arg Arg
         35                  40                  45
Ser Thr Gln Gly Thr Val Ser Glu Val Leu Gly Lys Ala Phe Val Ser
     50                  55                  60
Phe Asp Lys Asp Ile Arg Gln Asn Tyr Trp Pro Asp Ser Ile Arg Ala
65                  70                  75                  80
```

```
        Gln   Ile   Ala   Ser   Leu   Ser   Ala   Glu   Asp   Lys   Ser   Ile   Leu   Gln   Gly   Tyr
                          85                            90                            95

Ala   Asp   Gly   Met   Asn   Ala   Trp   Ile   Asp   Lys   Val   Asn   Ala   Ser   Pro   Asp
                          100                           105                           110

Lys   Leu   Leu   Pro   Gln   Gln   Phe   Ser   Thr   Phe   Gly   Phe   Lys   Pro   Lys   His
                          115                           120                           125

Trp   Glu   Pro   Phe   Asp   Val   Ala   Met   Ile   Phe   Val   Gly   Thr   Met   Ala   Asn
                    130                           135                           140

Arg   Phe   Ser   Asp   Ser   Thr   Ser   Glu   Ile   Asp   Asn   Leu   Ala   Leu   Leu   Thr
        145                                 150                           155                           160

Ala   Val   Lys   Asp   Lys   Tyr   Gly   Asn   Asp   Glu   Gly   Met   Ala   Val   Phe   Asn
                                165                           170                           175

Gln   Leu   Lys   Trp   Leu   Val   Asn   Pro   Ser   Ala   Pro   Thr   Thr   Ile   Ala   Ala
                          180                           185                           190

Arg   Glu   Ser   Ser   Tyr   Pro   Leu   Lys   Phe   Asp   Leu   Gln   Asn   Thr   Gln   Thr
                          195                           200                           205

Ala
```

( 2 ) INFORMATION FOR SEQ ID NO:30:

( i ) SEQUENCE CHARACTERISTICS:
        ( A ) LENGTH: 207 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:30:

```
        Ala   Lys   Asn   Glu   Gly   Val   Lys   Val   Val   Arg   Asp   Asn   Phe   Gly   Val   Pro
        1                       5                             10                            15

His   Leu   Tyr   Ala   Lys   Asn   Lys   Lys   Asp   Leu   Tyr   Glu   Ala   Tyr   Gly   Tyr
                          20                            25                            30

Val   Met   Ala   Lys   Asp   Arg   Leu   Phe   Gln   Leu   Glu   Met   Phe   Arg   Arg   Gly
                    35                            40                            45

Asn   Glu   Gly   Thr   Val   Ser   Glu   Ile   Phe   Gly   Glu   Asp   Tyr   Leu   Ser   Lys
              50                            55                            60

Asp   Glu   Gln   Ser   Arg   Arg   Asp   Gly   Tyr   Ser   Asn   Lys   Glu   Ile   Lys   Lys
        65                            70                            75                            80

Met   Ile   Asp   Gly   Leu   Asp   Arg   Gln   Pro   Arg   Glu   Leu   Ile   Ala   Lys   Phe
                          85                            90                            95

Ala   Glu   Gly   Ile   Ser   Arg   Tyr   Val   Asn   Glu   Ala   Leu   Lys   Asp   Pro   Asp
                          100                           105                           110

Asp   Lys   Leu   Ser   Lys   Glu   Phe   His   Glu   Tyr   Gln   Phe   Leu   Pro   Gln   Lys
                          115                           120                           125

Trp   Thr   Ser   Thr   Asp   Val   Val   Arg   Val   Tyr   Met   Val   Ser   Met   Thr   Tyr
                    130                           135                           140

Leu   Trp   Ile   Ile   Thr   Arg   Glu   Leu   Lys   Asn   Ala   Glu   Ile   Leu   Ala   Lys
        145                                 150                           155                           160

Leu   Glu   His   Glu   Tyr   Gly   Thr   Glu   Val   Ser   Arg   Lys   Met   Phe   Asp   Asp
                          165                           170                           175

Leu   Val   Trp   Lys   Asn   Asp   Pro   Ser   Ala   Pro   Thr   Ser   Ile   Val   Ser   Glu
                          180                           185                           190

Gly   Lys   Pro   Lys   Arg   Glu   Ser   Ser   Gln   Ser   Leu   Gln   Lys   Leu
                          195                           200                           205
```

5,891,703

47

-continued

48

( 2 ) INFORMATION FOR SEQ ID NO:31:

( i ) SEQUENCE CHARACTERISTICS:
        ( A ) LENGTH: 284 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:31:

```
Met Lys Lys His Leu Ile Ser Ile Ala Ile Val Leu Ser Leu Ser Ser
 1               5                  10                  15
Leu Ser Leu Ser Ser Phe Ser Gln Ser Thr Gln Ile Lys Ile Glu Arg
            20                  25                  30
Asp Asn Tyr Gly Val Pro His Ile Tyr Ala Asn Asp Thr Tyr Ser Leu
        35                  40                  45
Phe Tyr Gly Tyr Gly Tyr Ala Val Ala Gln Asp Arg Leu Phe Gln Met
    50                  55                  60
Glu Met Ala Lys Arg Ser Thr Gln Gly Thr Val Ser Glu Val Phe Gly
65                  70                  75                  80
Lys Asp Tyr Ile Ser Phe Asp Lys Glu Ile Arg Asn Asn Tyr Trp Pro
                85                  90                  95
Asp Ser Ile His Lys Gln Ile Asn Gln Leu Pro Ser Gln Glu Gln Asp
            100                 105                 110
Ile Leu Arg Gly Tyr Ala Asp Gly Met Asn Ala Trp Ile Lys Gln Ile
        115                 120                 125
Asn Thr Lys Pro Asp Asp Leu Met Pro Lys Gln Phe Ile Asp Tyr Asp
    130                 135                 140
Phe Leu Pro Ser Gln Trp Thr Ser Phe Asp Val Ala Met Ile Met Val
145                 150                 155                 160
Gly Thr Met Ala Asn Arg Phe Ser Asp Met Asn Ser Glu Ile Asp Asn
                165                 170                 175
Leu Ala Leu Leu Thr Ala Leu Lys Asp Lys Tyr Gly Glu Gln Leu Gly
            180                 185                 190
Val Glu Phe Phe Asn Gln Ile Asn Trp Leu Asn Asn Pro Asn Ala Pro
        195                 200                 205
Thr Thr Ile Ser Ser Glu Glu Phe Thr Tyr Ser Asp Ser Gln Lys Thr
    210                 215                 220
Lys Asn Ile Ser Gln Leu Asn Gln Ile Ser Asp Tyr Arg Leu Thr Ala
225                 230                 235                 240
Pro Met Phe Glu Arg Thr Ala Lys Asp Thr Thr Gly Lys Val Leu Ala
                245                 250                 255
Leu Ser Ser Gln Glu Asn Asn Ala Leu Ile Ala Lys Gln Tyr Glu Gln
            260                 265                 270
Ser Gly Ala Asn Gly Leu Ala Gly Tyr Pro Thr Thr
        275                 280
```

( 2 ) INFORMATION FOR SEQ ID NO:32:

( i ) SEQUENCE CHARACTERISTICS:
        ( A ) LENGTH: 551 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:32:

```
Ser Asn Leu Trp Ser Thr Arg Pro Glu Arg Val Gln Glu Gly Ser Thr
```

-continued

```
  1                   5                           10                        15
Val  Leu  Ile  Asn  Gly  Pro  Gln  Phe  Gly  Trp  Tyr  Asn  Pro  Tyr  Thr
               20                  25                       30

Tyr  Gly  Ile  Gly  Leu  His  Gly  Ala  Gly  Phe  Asp  Val  Val  Gly  Asn  Thr
                35                       40                  45

Pro  Phe  Ala  Tyr  Pro  Ile  Val  Leu  Phe  Gly  Thr  Asn  Ser  Glu  Ile  Ala
               50                  55                       60

Trp  Gly  Ala  Thr  Ala  Gly  Pro  Gln  Asp  Val  Val  Asp  Ile  Tyr  Gln  Glu
65                       70                  75                            80

Lys  Leu  Asn  Pro  Ser  Arg  Ala  Asp  Gln  Tyr  Trp  Phe  Asn  Asn  Ala  Trp
                    85                  90                       95

Arg  Thr  Met  Glu  Gln  Arg  Lys  Glu  Arg  Ile  Gln  Val  Arg  Gly  Gln  Ala
               100                 105                      110

Asp  Arg  Glu  Met  Thr  Ile  Trp  Arg  Thr  Val  His  Gly  Pro  Val  Met  Gln
               115                 120                      125

Phe  Asp  Tyr  Asp  Gln  Gly  Ala  Ala  Tyr  Ser  Lys  Lys  Arg  Ser  Trp  Asp
               130                 135                      140

Gly  Tyr  Glu  Val  Gln  Ser  Leu  Leu  Ala  Trp  Leu  Asn  Val  Ala  Lys  Ala
145                      150                 155                           160

Arg  Asn  Trp  Thr  Glu  Phe  Leu  Asp  Gln  Ala  Ser  Lys  Met  Ala  Ile  Ser
               165                 170                      175

Ile  Asn  Trp  Tyr  Tyr  Ala  Asp  Lys  His  Gly  Asn  Ile  Gly  Tyr  Val  Ser
               180                 185                      190

Pro  Ala  Phe  Leu  Pro  Gln  Arg  Pro  Ala  Asp  Gln  Asp  Ile  Arg  Val  Pro
               195                 200                      205

Ala  Lys  Gly  Asp  Gly  Ser  Met  Glu  Trp  Leu  Gly  Ile  Lys  Ser  Phe  Asp
     210                 215                      220

Ala  Ile  Pro  Lys  Ala  Tyr  Asn  Pro  Pro  Gln  Gly  Tyr  Leu  Val  Asn  Trp
225                      230                 235                           240

Asn  Asn  Lys  Pro  Ala  Pro  Asp  Lys  Thr  Asn  Thr  Asp  Thr  Tyr  Tyr  Trp
                    245                 250                      255

Thr  Tyr  Gly  Asp  Arg  Met  Asn  Glu  Leu  Val  Ser  Gln  Tyr  Gln  Gln  Lys
               260                 265                      270

Asp  Leu  Phe  Ser  Val  Gln  Glu  Ile  Trp  Glu  Phe  Asn  Gln  Lys  Ala  Ser
               275                 280                      285

Tyr  Ser  Asp  Val  Asn  Trp  Arg  Tyr  Phe  Arg  Pro  His  Leu  Glu  Lys  Leu
     290                 295                      300

Ala  Gln  Gln  Leu  Pro  Ala  Asp  Asp  Ser  Ser  Lys  Ala  Ala  Leu  Thr  Met
305                      310                 315                           320

Leu  Leu  Ala  Trp  Asp  Gly  Met  Glu  Gln  Asp  Gln  Gly  Gly  Gln  Asn  Ala
               325                 330                      335

Gly  Pro  Ala  Arg  Val  Leu  Phe  Lys  Thr  Trp  Leu  Glu  Glu  Met  Tyr  Lys
               340                 345                      350

Gln  Val  Leu  Met  Pro  Val  Val  Pro  Glu  Ser  His  Arg  Ala  Met  Tyr  Ser
               355                 360                      365

Gln  Thr  Gly  Phe  Ala  Thr  Gln  Gln  Gly  Pro  Asn  Pro  Gly  Ser  Ile  Asn
               370                 375                      380

Leu  Ser  Met  Gly  Thr  Lys  Val  Leu  Leu  Arg  Ala  Leu  Val  Leu  Glu  Ala
385                      390                 395                           400

His  Pro  Asp  Pro  Lys  Arg  Val  Asn  Val  Phe  Gly  Glu  Arg  Ser  Ser  Gln
                    405                 410                      415

Glu  Ile  Met  His  Thr  Ala  Leu  Gln  Asn  Ala  Gln  Ala  Arg  Leu  Ser  Gln
               420                 425                      430
```

| Glu | Gln | Gly | Ala | Gln | Met | Ala | Arg | Trp | Thr | Met | Pro | Thr | Ser | Val | His |
|---|---|---|---|---|---|---|---|---|---|---|---|---|---|---|---|
| | | 435 | | | | | 440 | | | | | 445 | | | |

| Arg | Phe | Ser | Asp | Lys | Asn | Phe | Thr | Gly | Thr | Pro | Gln | Thr | Met | Pro | Gly |
|---|---|---|---|---|---|---|---|---|---|---|---|---|---|---|---|
| | 450 | | | | | 455 | | | | | 460 | | | | |

| Asn | Thr | Phe | Ala | Phe | Thr | Gly | Tyr | Gln | Asn | Arg | Gly | Thr | Glu | Asn | Asn |
|---|---|---|---|---|---|---|---|---|---|---|---|---|---|---|---|
| 465 | | | | | 470 | | | | | 475 | | | | | 480 |

| Arg | Val | Val | Phe | Asp | Ala | Lys | Gly | Val | Glu | Phe | Cys | Asp | Ala | Met | Pro |
|---|---|---|---|---|---|---|---|---|---|---|---|---|---|---|---|
| | | | | 485 | | | | | 490 | | | | | 495 | |

| Pro | Gly | Gln | Ser | Gly | Phe | Thr | Asp | Arg | Asn | Gly | Val | Arg | Ser | Pro | His |
|---|---|---|---|---|---|---|---|---|---|---|---|---|---|---|---|
| | | | 500 | | | | | 505 | | | | | 510 | | |

| Tyr | Glu | Asp | Gln | Leu | Lys | Leu | Tyr | Glu | Asn | Phe | Glu | Cys | Lys | Thr | Met |
|---|---|---|---|---|---|---|---|---|---|---|---|---|---|---|---|
| | | | 515 | | | | 520 | | | | | 525 | | | |

| Asp | Val | Thr | His | Ala | Asp | Ile | Arg | Arg | Asn | Ala | Gln | Ser | Ser | Thr | Met |
|---|---|---|---|---|---|---|---|---|---|---|---|---|---|---|---|
| | | 530 | | | | 535 | | | | | 540 | | | | |

| Leu | Leu | Ile | Gln | Pro | Gln | Pro |
|---|---|---|---|---|---|---|
| 545 | | | | | 550 | |

( 2 ) INFORMATION FOR SEQ ID NO:33:

( i ) SEQUENCE CHARACTERISTICS:
        ( A ) LENGTH: 557 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:33:

| Ser | Asn | Met | Trp | Val | Ile | Gly | Lys | Ser | Lys | Ala | Gln | Asp | Ala | Lys | Ala |
|---|---|---|---|---|---|---|---|---|---|---|---|---|---|---|---|
| 1 | | | | 5 | | | | | 10 | | | | | 15 | |

| Ile | Met | Val | Asn | Gly | Pro | Gln | Phe | Gly | Trp | Tyr | Ala | Pro | Ala | Tyr | Thr |
|---|---|---|---|---|---|---|---|---|---|---|---|---|---|---|---|
| | | | 20 | | | | 25 | | | | | 30 | | | |

| Tyr | Gly | Ile | Gly | Leu | His | Gly | Ala | Gly | Tyr | Asp | Val | Thr | Gly | Asn | Thr |
|---|---|---|---|---|---|---|---|---|---|---|---|---|---|---|---|
| | | | 35 | | | | 40 | | | | | 45 | | | |

| Pro | Phe | Ala | Tyr | Pro | Gly | Leu | Gly | Phe | Gly | His | Asn | Gly | Val | Ile | Ser |
|---|---|---|---|---|---|---|---|---|---|---|---|---|---|---|---|
| | 50 | | | | | 55 | | | | | 60 | | | | |

| Trp | Gly | Ser | Thr | Ala | Gly | Phe | Gly | Asp | Asp | Val | Asp | Ile | Phe | Ala | Glu |
|---|---|---|---|---|---|---|---|---|---|---|---|---|---|---|---|
| 65 | | | | | 70 | | | | | 75 | | | | | 80 |

| Arg | Leu | Ser | Ala | Glu | Lys | Pro | Gly | Tyr | Tyr | Leu | His | Asn | Gly | Lys | Trp |
|---|---|---|---|---|---|---|---|---|---|---|---|---|---|---|---|
| | | | | 85 | | | | | 90 | | | | | 95 | |

| Val | Lys | Met | Leu | Ser | Arg | Glu | Glu | Thr | Ile | Thr | Val | Lys | Asn | Gly | Gln |
|---|---|---|---|---|---|---|---|---|---|---|---|---|---|---|---|
| | | | 100 | | | | | 105 | | | | | 110 | | |

| Ala | Glu | Thr | Phe | Thr | Val | Trp | Arg | Thr | Val | His | Gly | Asn | Ile | Leu | Gln |
|---|---|---|---|---|---|---|---|---|---|---|---|---|---|---|---|
| | | | 115 | | | | | 120 | | | | | 125 | | |

| Thr | Asp | Gln | Thr | Thr | Gln | Thr | Ala | Tyr | Ala | Lys | Ser | Arg | Ala | Trp | Asp |
|---|---|---|---|---|---|---|---|---|---|---|---|---|---|---|---|
| | 130 | | | | | 135 | | | | | 140 | | | | |

| Gly | Lys | Glu | Val | Ala | Ser | Leu | Leu | Ala | Trp | Thr | His | Gln | Met | Lys | Ala |
|---|---|---|---|---|---|---|---|---|---|---|---|---|---|---|---|
| 145 | | | | | 150 | | | | | 155 | | | | | 160 |

| Lys | Asn | Trp | Gln | Glu | Trp | Thr | Gln | Gln | Ala | Ala | Lys | Gln | Ala | Leu | Thr |
|---|---|---|---|---|---|---|---|---|---|---|---|---|---|---|---|
| | | | | 165 | | | | | 170 | | | | | 175 | |

| Ile | Asn | Trp | Tyr | Tyr | Ala | Asp | Val | Asn | Gly | Asn | Ile | Gly | Tyr | Val | His |
|---|---|---|---|---|---|---|---|---|---|---|---|---|---|---|---|
| | | | | 180 | | | | | 185 | | | | | 190 | |

| Thr | Gly | Ala | Tyr | Pro | Asp | Arg | Gln | Ser | Gly | His | Asp | Pro | Arg | Leu | Pro |
|---|---|---|---|---|---|---|---|---|---|---|---|---|---|---|---|
| | | | 195 | | | | | 200 | | | | | 205 | | |

| Val | Pro | Gly | Thr | Gly | Lys | Trp | Asp | Trp | Lys | Gly | Leu | Leu | Pro | Phe | Glu |
|---|---|---|---|---|---|---|---|---|---|---|---|---|---|---|---|
| | 210 | | | | | 215 | | | | | 220 | | | | |

| Met | Asn | Pro | Lys | Val | Tyr | Asn | Pro | Gln | Ser | Gly | Tyr | Ile | Ala | Asn | Trp |

```
              225                      230                       235                      240

Asn  Asn  Ser  Pro  Gln  Lys  Asp  Tyr  Pro  Ala  Ser  Asp  Leu  Phe  Ala  Phe
                        245                      250                      255

Leu  Trp  Gly  Gly  Ala  Asp  Arg  Val  Thr  Glu  Ile  Asp  Arg  Leu  Leu  Glu
                   260                      265                      270

Gln  Lys  Pro  Arg  Leu  Thr  Ala  Asp  Gln  Ala  Trp  Asp  Val  Ile  Arg  Gln
              275                      280                      285

Thr  Ser  Arg  Gln  Asp  Leu  Asn  Leu  Arg  Leu  Phe  Leu  Pro  Thr  Leu  Gln
         290                      295                      300

Ala  Ala  Thr  Ser  Gly  Leu  Thr  Gln  Ser  Pro  Pro  Arg  Arg  Gln  Leu  Val
    305                      310                      315                      320

Glu  Thr  Leu  Thr  Arg  Trp  Asp  Gly  Ile  Asn  Leu  Leu  Asn  Asp  Asp  Gly
                        325                      330                      335

Lys  Thr  Trp  Gln  Gln  Pro  Gly  Ser  Ala  Ile  Leu  Asn  Val  Trp  Leu  Thr
                   340                      345                      350

Ser  Met  Leu  Lys  Arg  Thr  Val  Val  Ala  Ala  Val  Pro  Met  Pro  Phe  Asp
                   355                      360                      365

Lys  Trp  Tyr  Ser  Ala  Ser  Gly  Tyr  Glu  Thr  Thr  Gln  Asp  Gly  Pro  Thr
              370                      375                      380

Gly  Ser  Leu  Asn  Ile  Ser  Val  Gly  Ala  Lys  Ile  Leu  Tyr  Glu  Ala  Val
    385                      390                      395                      400

Gln  Gly  Asp  Lys  Ser  Pro  Ile  Pro  Gln  Ala  Val  Asp  Leu  Phe  Ala  Gly
                        405                      410                      415

Lys  Pro  Gln  Gln  Glu  Val  Val  Leu  Ala  Ala  Leu  Glu  Asp  Thr  Trp  Glu
                   420                      425                      430

Thr  Leu  Ser  Lys  Arg  Tyr  Gly  Asn  Asn  Val  Ser  Asn  Trp  Lys  Thr  Pro
              435                      440                      445

Ala  Met  Ala  Leu  Thr  Phe  Arg  Ala  Asn  Asn  Phe  Phe  Gly  Val  Pro  Gln
         450                      455                      460

Ala  Ala  Ala  Glu  Glu  Thr  Arg  His  Gln  Ala  Glu  Tyr  Gln  Asn  Arg  Gly
    465                      470                      475                      480

Thr  Glu  Asn  Asp  Met  Ile  Val  Phe  Ser  Pro  Thr  Thr  Ser  Asp  Arg  Pro
                        485                      490                      495

Val  Leu  Ala  Trp  Asp  Val  Val  Ala  Pro  Gly  Gln  Ser  Gly  Phe  Ile  Ala
                   500                      505                      510

Pro  Asp  Gly  Thr  Val  Asp  Lys  His  Tyr  Glu  Asp  Gln  Leu  Lys  Met  Tyr
                   515                      520                      525

Glu  Asn  Phe  Gly  Arg  Lys  Ser  Leu  Trp  Leu  Thr  Lys  Gln  Asp  Val  Glu
              530                      535                      540

Ala  His  Lys  Glu  Ser  Gln  Glu  Val  Leu  His  Val  Gln  Arg
    545                      550                      555
```

( 2 ) INFORMATION FOR SEQ ID NO:34:

( i ) SEQUENCE CHARACTERISTICS:
        ( A ) LENGTH: 555 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:34:

```
    Ser  Asn  Met  Trp  Val  Ile  Gly  Lys  Asn  Lys  Ala  Gln  Asp  Ala  Lys  Ala
    1                   5                        10                       15

Ile  Met  Val  Asn  Gly  Pro  Gln  Phe  Gly  Trp  Tyr  Ala  Pro  Ala  Tyr  Thr
                   20                       25                       30
```

|   |   |   |   |   |   |   |   |   |   |   |   |   |   |
|---|---|---|---|---|---|---|---|---|---|---|---|---|---|
| Tyr | Gly | Ile 35 | Gly | Leu | His | Gly | Ala 40 | Gly | Tyr | Asp | Val | Thr 45 | Gly | Asn | Thr |
| Pro | Phe 50 | Ala | Tyr | Pro | Gly 55 | Leu | Val | Phe | Gly | His 60 | Asn | Gly | Thr | Ile | Ser |
| Trp 65 | Gly | Ser | Thr | Ala 70 | Gly | Phe | Gly | Asp | Asp 75 | Val | Asp | Ile | Phe | Ala | Glu 80 |
| Lys | Leu | Ser | Ala | Glu 85 | Lys | Pro | Gly | Tyr | Tyr 90 | Gln | His | Asn | Gly | Glu 95 | Trp |
| Val | Lys | Met | Leu 100 | Ser | Arg | Lys | Glu | Thr 105 | Ile | Ala | Val | Lys | Asp 110 | Gly | Gln |
| Pro | Glu | Thr 115 | Phe | Thr | Val | Trp | Arg 120 | Thr | Leu | Asp | Gly | Asn 125 | Val | Ile | Lys |
| Thr | Asp 130 | Thr | Arg | Thr | Gln | Thr 135 | Ala | Tyr | Ala | Lys | Ala 140 | Arg | Ala | Trp | Ala |
| Gly 145 | Lys | Glu | Val | Ala | Ala 150 | Leu | Leu | Ala | Trp | Thr 155 | His | Gln | Met | Lys | Ala 160 |
| Lys | Asn | Trp | Pro | Glu 165 | Trp | Thr | Gln | Gln | Ala 170 | Ala | Lys | Gln | Ala | Leu 175 | Thr |
| Ile | Asn | Trp | Tyr 180 | Tyr | Ala | Asp | Val | Asn 185 | Gly | Asn | Ile | Gly | Tyr 190 | Val | His |
| Thr | Gly | Ala 195 | Tyr | Pro | Asp | Arg | Gln 200 | Pro | Gly | His | Asp | Pro 205 | Arg | Leu | Pro |
| Val | Pro 210 | Asp | Gly | Lys | Trp | Asp 215 | Trp | Lys | Gly | Leu | Leu 220 | Ser | Phe | Asp | Leu |
| Asn 225 | Pro | Lys | Val | Tyr | Asn 230 | Pro | Gln | Ser | Gly | Tyr 235 | Ile | Ala | Asn | Trp | Asn 240 |
| Asn | Ser | Pro | Gln | Lys 245 | Asp | Tyr | Pro | Ala | Ser 250 | Asp | Leu | Phe | Ala | Phe 255 | Leu |
| Trp | Gly | Gly | Ala 260 | Asp | Arg | Val | Thr | Glu 265 | Ile | Asp | Thr | Ile | Leu 270 | Asp | Lys |
| Gln | Pro | Arg 275 | Phe | Thr | Ala | Asp | Gln 280 | Ala | Trp | Asp | Val | Ile 285 | Arg | Gln | Thr |
| Ser | Leu 290 | Arg | Asp | Leu | Leu | Arg 295 | Leu | Phe | Leu | Pro | Ala 300 | Leu | Lys | Asp | Ala |
| Thr 305 | Ala | Asn | Leu | Ala | Glu 310 | Asn | Asp | Pro | Arg | Arg 315 | Gln | Leu | Val | Asp | Lys 320 |
| Leu | Ala | Ser | Trp | Asp 325 | Gly | Glu | Asn | Leu | Val 330 | Asn | Asp | Asp | Gly | Lys 335 | Thr |
| Tyr | Gln | Gln | Pro 340 | Gly | Ser | Ala | Ile | Leu 345 | Asn | Ala | Trp | Leu | Thr 350 | Ser | Met |
| Leu | Lys | Arg 355 | Thr | Leu | Val | Ala | Ala 360 | Val | Pro | Ala | Pro | Phe 365 | Gly | Lys | Trp |
| Tyr | Ser 370 | Ala | Ser | Gly | Tyr | Glu 375 | Thr | Thr | Gln | Asp | Gly 380 | Pro | Thr | Gly | Ser |
| Leu 385 | Asn | Ile | Ser | Val | Gly 390 | Ala | Lys | Ile | Leu | Tyr 395 | Glu | Ala | Leu | Gln | Gly 400 |
| Asp | Lys | Ser | Pro | Ile 405 | Pro | Gln | Ala | Val | Asp 410 | Leu | Phe | Gly | Gly | Lys 415 | Pro |
| Glu | Gln | Glu | Val 420 | Ile | Leu | Ala | Ala | Leu 425 | Asp | Asp | Ala | Trp | Gln 430 | Thr | Leu |
| Ser | Lys | Arg 435 | Tyr | Gly | Asn | Asp | Val 440 | Thr | Gly | Trp | Lys | Thr 445 | Pro | Ala | Met |
| Ala | Leu | Thr | Phe | Arg | Ala | Asn | Asn | Phe | Phe | Gly | Val | Pro | Gln | Ala | Ala |

|  | 450 |  |  |  | 455 |  |  |  | 460 |  |  |  |  |  |
|---|---|---|---|---|---|---|---|---|---|---|---|---|---|---|
| Ala | Lys | Glu | Ala | Arg | His | Gln | Ala | Glu | Tyr | Gln | Asn | Arg | Gly | Thr | Glu |
| 465 |  |  |  |  | 470 |  |  |  |  | 475 |  |  |  |  | 480 |
| Asn | Asp | Met | Ile | Val | Phe | Ser | Pro | Thr | Ser | Gly | Asn | Arg | Pro | Val | Leu |
|  |  |  |  | 485 |  |  |  |  | 490 |  |  |  |  | 495 |  |
| Ala | Trp | Asp | Val | Val | Ala | Pro | Gly | Gln | Ser | Gly | Phe | Ile | Ala | Pro | Asp |
|  |  |  | 500 |  |  |  |  | 505 |  |  |  |  | 510 |  |  |
| Gly | Lys | Ala | Asp | Lys | His | Tyr | Asp | Asp | Gln | Leu | Lys | Met | Tyr | Glu | Ser |
|  |  | 515 |  |  |  |  | 520 |  |  |  |  | 525 |  |  |  |
| Phe | Gly | Arg | Lys | Ser | Leu | Trp | Leu | Thr | Pro | Gln | Asp | Val | Asp | Glu | His |
|  | 530 |  |  |  |  | 535 |  |  |  |  | 540 |  |  |  |  |
| Lys | Glu | Ser | Gln | Glu | Val | Leu | Gln | Val | Gln | Arg |  |  |  |  |  |
| 545 |  |  |  | 550 |  |  |  |  | 555 |  |  |  |  |  |  |

( 2 ) INFORMATION FOR SEQ ID NO:35:

( i ) SEQUENCE CHARACTERISTICS:
        ( A ) LENGTH: 528 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:35:

| Ser | Asn | Ala | Ala | Ile | Val | Gly | Ser | Glu | Lys | Ser | Ala | Thr | Gly | Asn | Ala |
|---|---|---|---|---|---|---|---|---|---|---|---|---|---|---|---|
| 1 |  |  |  | 5 |  |  |  |  | 10 |  |  |  |  | 15 |  |
| Leu | Leu | Phe | Ser | Gly | Pro | Gln | Val | Gly | Phe | Val | Ala | Pro | Gly | Phe | Leu |
|  |  |  | 20 |  |  |  |  | 25 |  |  |  |  | 30 |  |  |
| Tyr | Glu | Val | Gly | Leu | His | Ala | Pro | Gly | Phe | Asp | Met | Glu | Gly | Ser | Gly |
|  |  | 35 |  |  |  |  | 40 |  |  |  |  | 45 |  |  |  |
| Phe | Ile | Gly | Tyr | Pro | Phe | Ile | Met | Phe | Gly | Ala | Asn | Asn | His | Phe | Ala |
|  | 50 |  |  |  |  | 55 |  |  |  |  | 60 |  |  |  |  |
| Leu | Ser | Ala | Thr | Ala | Gly | Tyr | Gly | Asn | Val | Thr | Asp | Ile | Phe | Glu | Glu |
| 65 |  |  |  |  | 70 |  |  |  |  | 75 |  |  |  |  | 80 |
| Lys | Leu | Asn | Thr | Lys | Asn | Ser | Ser | Gln | Tyr | Leu | Tyr | Lys | Gly | Lys | Trp |
|  |  |  |  | 85 |  |  |  |  | 90 |  |  |  |  | 95 |  |
| Arg | Asp | Met | Glu | Lys | Arg | Lys | Glu | Ser | Phe | Thr | Val | Lys | Gly | Asp | Asn |
|  |  |  | 100 |  |  |  |  | 105 |  |  |  |  | 110 |  |  |
| Gly | Glu | Lys | Lys | Thr | Val | Glu | Lys | Ile | Tyr | Tyr | Arg | Thr | Val | His | Gly |
|  |  | 115 |  |  |  |  | 120 |  |  |  |  | 125 |  |  |  |
| Pro | Val | Ile | Ser | Arg | Asp | Glu | Thr | Asn | Lys | Val | Ala | Tyr | Ser | Lys | Tyr |
|  | 130 |  |  |  |  | 135 |  |  |  |  | 140 |  |  |  |  |
| Val | Ser | Phe | Arg | Gly | Thr | Glu | Glu | Ala | Gln | Ser | Met | Ser | Ala | Tyr | Met |
| 145 |  |  |  |  | 150 |  |  |  |  | 155 |  |  |  |  | 160 |
| Lys | Ala | Asn | Trp | Ala | Lys | Asn | Leu | Lys | Glu | Phe | Glu | Asn | Ala | Ala | Ser |
|  |  |  |  | 165 |  |  |  |  | 170 |  |  |  |  | 175 |  |
| Glu | Tyr | Thr | Met | Ser | Leu | Asn | Trp | Tyr | Tyr | Ala | Asp | Lys | Lys | Gly | Asp |
|  |  |  | 180 |  |  |  |  | 185 |  |  |  |  | 190 |  |  |
| Ile | Ala | Tyr | Tyr | His | Val | Gly | Arg | Tyr | Pro | Val | Arg | Asn | Asn | Lys | Ile |
|  |  | 195 |  |  |  |  | 200 |  |  |  |  | 205 |  |  |  |
| Asp | Glu | Arg | Ile | Pro | Thr | Pro | Gly | Thr | Gly | Glu | Tyr | Glu | Trp | Lys | Gly |
|  | 210 |  |  |  |  | 215 |  |  |  |  | 220 |  |  |  |  |
| Phe | Ile | Pro | Phe | Lys | Glu | Asn | Pro | His | Val | Ile | Asn | Pro | Lys | Asn | Gly |
| 225 |  |  |  |  | 230 |  |  |  |  | 235 |  |  |  |  | 240 |
| Tyr | Val | Val | Asn | Trp | Asn | Asn | Lys | Pro | Ser | Lys | Glu | Trp | Val | Asn | Gly |
|  |  |  |  | 245 |  |  |  |  | 250 |  |  |  |  | 255 |  |

|   |   |   |   |   |   |   |   |   |   |   |   |   |   |   |
|---|---|---|---|---|---|---|---|---|---|---|---|---|---|---|
| Glu | Tyr | Ser | Tyr<br>260 | Tyr | Trp | Gly | Glu<br>265 | Asp | Asn | Arg | Val | Gln<br>270 | Gln | Tyr | Ile |
| Asn | Gly | Gly<br>275 | Met | Glu | Ala | Arg<br>280 | Gly | Lys | Val | Thr | Leu<br>285 | Glu | Asp | Ile | Asn |
| Glu | Ile<br>290 | Asn | Tyr | Thr | Ala | Ser<br>295 | Phe | Ala | Gln | Leu | Arg<br>300 | Ala | Asn | Leu | Phe |
| Lys<br>305 | Pro | Leu | Leu | Ile | Asp<br>310 | Val | Leu | Asp | Lys | Asn<br>315 | Lys | Ser | Thr | Asn | Gly<br>320 |
| Asn | Tyr | Thr | Tyr | Leu<br>325 | Ile | Glu | Lys | Leu | Glu<br>330 | Glu | Trp | Asn | Asn | Leu<br>335 | Lys |
| Glu | Asp | Glu | Asn<br>340 | Lys | Asp | Gly | Tyr | Tyr<br>345 | Asp | Ala | Gly | Ile | Ala<br>350 | Ala | Phe |
| Phe | Asp | Glu<br>355 | Trp | Trp | Asn | Asn | Leu<br>360 | His | Asp | Lys | Leu | Phe<br>365 | Met | Asp | Glu |
| Leu | Gly<br>370 | Asp | Phe | Tyr | Gly | Ile<br>375 | Thr | Lys | Glu | Ile | Thr<br>380 | Asp | His | Arg | Tyr |
| Gly<br>385 | Ala | Ser | Leu | Ala | Tyr<br>390 | Lys | Asn | Ile | Ser | Lys<br>395 | Glu | Ser | Thr | Asn | Tyr<br>400 |
| Lys | Trp | Val | Lys | Trp<br>405 | Val | Asn | Val | Asp | Gln<br>410 | Glu | Lys | Ile | Ile | Met<br>415 | Glu |
| Ser | Thr | Asn | Glu<br>420 | Val | Leu | Ala | Lys | Leu<br>425 | Gln | Ser | Glu | Lys | Gly<br>430 | Leu | Lys |
| Ala | Glu | Lys<br>435 | Trp | Arg | Met | Pro | Ile<br>440 | Lys | Thr | Met | Thr | Phe<br>445 | Gly | Glu | Lys |
| Ser | Leu<br>450 | Ile | Gly | Ile | Pro | His<br>455 | Gly | Tyr | Gly | Ser | Met<br>460 | Thr | Pro | Ile | Ile |
| Glu<br>465 | Met | Asn | Arg | Gly | Ser<br>470 | Glu | Asn | His | Tyr | Ile<br>475 | Glu | Met | Thr | Pro | Lys<br>480 |
| Gly | Pro | Ser | Gly | Phe<br>485 | Asn | Ile | Thr | Pro | Pro<br>490 | Gly | Gln | Ile | Gly | Phe<br>495 | Val |
| Lys | Lys | Asp | Gly<br>500 | Thr | Ile | Ser | Asp | His<br>505 | Tyr | Asp | Asp | Gln | Leu<br>510 | Val | Met |
| Phe | Ala | Glu<br>515 | Trp | Lys | Phe | Lys | Pro<br>520 | Tyr | Leu | Phe | Asn | Lys<br>525 | Lys | Asp | Ile |

( 2 ) INFORMATION FOR SEQ ID NO:36:

( i ) SEQUENCE CHARACTERISTICS:
        ( A ) LENGTH: 553 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:36:

|   |   |   |   |   |   |   |   |   |   |   |   |   |   |   |
|---|---|---|---|---|---|---|---|---|---|---|---|---|---|---|
| Ser<br>1 | Asn | Val | Trp | Leu<br>5 | Val | Gly | Lys | Thr | Lys<br>10 | Ala | Ser | Gly | Ala | Lys<br>15 | Ala |
| Ile | Leu | Leu | Asn<br>20 | Gly | Pro | Gln | Phe | Gly<br>25 | Trp | Phe | Asn | Pro | Ala<br>30 | Tyr | Thr |
| Tyr | Gly | Ile<br>35 | Gly | Leu | His | Gly | Ala<br>40 | Gly | Phe | Asn | Ile | Val<br>45 | Gly | Asn | Thr |
| Pro | Phe<br>50 | Ala | Tyr | Pro | Ala | Ile<br>55 | Leu | Phe | Gly | His | Asn<br>60 | Gly | His | Val | Ser |
| Trp<br>65 | Gly | Ser | Thr | Ala | Gly<br>70 | Phe | Gly | Asp | Gly | Val<br>75 | Asp | Ile | Phe | Ala | Glu<br>80 |

-continued

| | | | | | | | | | | | | | | |
|---|---|---|---|---|---|---|---|---|---|---|---|---|---|---|
| Gln | Val | Ser | Pro | Glu | Asp | Pro | Asn | Ser | Tyr | Leu | His | Gln | Gly | Gln | Trp |
| | | | | 85 | | | | 90 | | | | | | 95 | |
| Lys | Lys | Met | Leu | Ser | Arg | Gln | Glu | Thr | Leu | Asn | Val | Lys | Gly | Glu | Gln |
| | | | 100 | | | | | 105 | | | | 110 | | | |
| Pro | Ile | Thr | Phe | Glu | Ile | Tyr | Arg | Thr | Val | His | Gly | Asn | Val | Val | Lys |
| | | 115 | | | | | | 120 | | | | 125 | | | |
| Arg | Asp | Lys | Thr | Thr | His | Thr | Ala | Tyr | Ser | Lys | Ala | Arg | Ala | Trp | Asp |
| | 130 | | | | | 135 | | | | | 140 | | | | |
| Gly | Lys | Glu | Leu | Thr | Ser | Leu | Met | Ala | Trp | Val | Lys | Gln | Gly | Gln | Ala |
| 145 | | | | | 150 | | | | | 155 | | | | | 160 |
| Gln | Asn | Trp | Gln | Gln | Trp | Leu | Asp | Gln | Ala | Gln | Asn | Gln | Ala | Leu | Thr |
| | | | | 165 | | | | 170 | | | | | 175 | | |
| Ile | Asn | Trp | Tyr | Tyr | Ala | Asp | Lys | Asp | Gly | Asn | Ile | Gly | Tyr | Val | His |
| | | | 180 | | | | | 185 | | | | 190 | | | |
| Thr | Gly | His | Tyr | Pro | Asp | Arg | Gln | Ile | Asn | His | Asp | Pro | Arg | Leu | Pro |
| | | 195 | | | | | 200 | | | | | 205 | | | |
| Val | Ser | Gly | Thr | Gly | Glu | Trp | Asp | Trp | Lys | Gly | Ile | Gln | Pro | Phe | Ala |
| | 210 | | | | | 215 | | | | | 220 | | | | |
| Asn | Asn | Pro | Lys | Val | Tyr | Asn | Pro | Lys | Ser | Gly | Tyr | Ile | Ala | Asn | Trp |
| 225 | | | | | 230 | | | | | 235 | | | | | 240 |
| Asn | Asn | Ser | Pro | Ala | Lys | Asn | Tyr | Pro | Ala | Ser | Asp | Leu | Phe | Ala | Phe |
| | | | | 245 | | | | 250 | | | | | 255 | | |
| Leu | Trp | Gly | Ser | Ala | Asp | Arg | Val | Lys | Glu | Ile | Asp | Asn | Arg | Ile | Glu |
| | | | 260 | | | | | 265 | | | | 270 | | | |
| Ala | Tyr | Asp | Lys | Leu | Thr | Ala | Asp | Asp | Met | Trp | Ala | Ile | Leu | Gln | Gln |
| | | 275 | | | | | 280 | | | | | 285 | | | |
| Thr | Ser | Arg | Val | Asp | Leu | Asn | His | Arg | Leu | Phe | Thr | Pro | Phe | Leu | Thr |
| | 290 | | | | | 295 | | | | | 300 | | | | |
| Gln | Ala | Thr | Gln | Gly | Leu | Pro | Ser | Asn | Asp | Asn | Ser | Val | Lys | Leu | Val |
| 305 | | | | | 310 | | | | | 315 | | | | | 320 |
| Ser | Met | Leu | Gln | Gln | Trp | Asp | Gly | Ile | Asn | Gln | Leu | Ser | Ser | Asp | Gly |
| | | | | 325 | | | | 330 | | | | | 335 | | |
| Lys | His | Tyr | Ile | His | Pro | Gly | Ser | Ala | Tyr | Leu | Asp | Ile | Trp | Leu | Lys |
| | | | 340 | | | | | 345 | | | | 350 | | | |
| Glu | Met | Leu | Lys | Ala | Thr | Leu | Gly | Gln | Thr | Val | Pro | Ala | Pro | Phe | Asp |
| | | 355 | | | | | 360 | | | | | 365 | | | |
| Lys | Trp | Tyr | Leu | Ala | Ser | Gly | Tyr | Glu | Thr | Thr | Gln | Glu | Gly | Pro | Thr |
| | 370 | | | | | 375 | | | | | 380 | | | | |
| Gly | Ser | Leu | Asn | Ile | Ser | Thr | Gly | Ala | Lys | Leu | Leu | Tyr | Glu | Ser | Leu |
| 385 | | | | | 390 | | | | | 395 | | | | | 400 |
| Leu | Glu | Asp | Lys | Ser | Pro | Ile | Ser | Gln | Ser | Ile | Asp | Leu | Phe | Ser | Gly |
| | | | | 405 | | | | 410 | | | | | 415 | | |
| Gln | Pro | Gln | Asn | Asp | Val | Ile | Arg | Lys | Thr | Leu | Asn | Thr | Thr | Tyr | Gln |
| | | | 420 | | | | | 425 | | | | 430 | | | |
| Lys | Met | Ile | Glu | Lys | Tyr | Gly | Asp | Asn | Pro | Ala | Asn | Trp | Gln | Thr | Pro |
| | | 435 | | | | | 440 | | | | | 445 | | | |
| Ala | Thr | Ala | Leu | Thr | Phe | Arg | Glu | Asn | Asn | Phe | Phe | Gly | Ile | Pro | Gln |
| | 450 | | | | | 455 | | | | | 460 | | | | |
| Ala | Leu | Pro | Gln | Glu | Asn | Phe | His | Gln | Asn | Glu | Tyr | His | Asn | Arg | Gly |
| 465 | | | | | 470 | | | | | 475 | | | | | 480 |
| Thr | Glu | Asn | Asp | Leu | Ile | Val | Phe | Thr | Glu | Glu | Gly | Val | Ser | Ala | Trp |
| | | | | 485 | | | | 490 | | | | | 495 | | |
| Asp | Val | Val | Ala | Pro | Gly | Gln | Ser | Gly | Phe | Ile | Ser | Pro | Gln | Gly | Lys |
| | | | 500 | | | | | 505 | | | | 510 | | | |

-continued

| Pro | Ser | Pro<br>515 | His | Tyr | Gln | Asp | Gln<br>520 | Leu | Ser | Leu | Tyr | Gln<br>525 | Gln | Phe | Gly |
| --- | --- | --- | --- | --- | --- | --- | --- | --- | --- | --- | --- | --- | --- | --- | --- |
| Lys | Lys<br>530 | Pro | Leu | Trp | Leu | Asn<br>535 | Ser | Glu | Asp | Val | Ala<br>540 | Pro | Tyr | Ile | Glu |
| Ser<br>545 | Thr | Glu | Thr | Leu | Ile<br>550 | Ile | Glu | Arg | | | | | | | |

What is claimed is:

1. An isolated mutant prokaryotic Penicillin G acylase or its preenzmye or preproenzyme having: an amino acid substitution at one or more of the positions corresponding to A139, A140, A142 and A148 to A152 as set forth in SEQ ID NO: 27, and B20 to B27, B31, B49 to B52, B56, B57, B65, B67 to B72, B154 to B157, B173 to B179, B239 to B241, B250 to B263, B379 to B387, B390, B455, and B474 to B480 as set forth in SEQ ID NO: 32 in *Alcaligenes faecalis* Penicillin G acylase or its pre- or preproenzyme; and an altered substrate specificity or altered specific activity relative to the corresponding wild-type unsubstituted Penicillin G acylase.

2. A mutant acylase according to claim 1, wherein said acylase is originated from *Alcaligenes faecalis*.

3. A mutant acylase according to claim 2 having an amino acid substitution at one or more of the positions A139, A140, A142 and 148 to A152 as set forth in SEQ ID NO: 27, and B22, B24, B25, B27, B31, B49, B52, B56, B57, B67, B68, B69, B70, B71, B154, B157, B173, B175, B176, B177, B179, B239, B240, B251, B253, B254, B255, B256, B261, B262, B379, B380, B381, B382, B383, B384, B390, B455, and B477 or B478 as set forth in SEQ ID NO: 32.

4. A mutant acylase according to claim 3, wherein the amino acid substitution is one of the following:

to Arg, Lys, Cys, Gly, Thr, Asp, Val, Leu or any other amino acid;

A147 (Phe)

B24 (Phe) as set forth in SEQ ID NO: 32 to Arg or Lys;

B56 (Leu) as set forth in SEQ ID NO: 32 to Arg, Lys, His, Gly, Ala or Val;

B177 (Ile) as set forth in SEQ ID NO: 32 to Arg, Lys, His, Val, Met, Ser or Thr;

B71 (Pro) as set forth in SEQ ID NO: 32 to Phe or Tyr; or

B67 (Ala), B68 (Thr) or B69 (Ala) as set forth in SEQ ID NO: 32 to any other amino acid.

5. A nucleic acid sequence encoding a mutant acylase as defined in any one of the preceding claims.

6. An expression vector comprising a nucleic acid sequence as defined in claim 5 operably linked to a promoter sequence capable of directing its expression in a host cell.

7. A microorganism transformed with an expression vector as defined in claim 6.

8. A microorganism according to claim 7, which is a microorganism of the genus Cephalosporium or the genus Penicillium.

9. A process of preparing an isolated mutant acylase as defined in any one of the claims 1–4, which process comprises:

culturing a microorganism as defined in claim 7 or 8, whereby said mutant acylase is produced; and isolating said acylase.

10. A method for deacylating a 6-acylated penicillanic acid, a 7-acylated (desacetoxy)cephalosporanic acid or a salt or ester thereof to form the corresponding 6-amino penicillanic acid or 7-amino(desacetoxy)cephalosporanic acid or salt or ester thereof, respectively, which comprises contacting said 6-acylated or 7-acylated compound with a mutant acylase as defined in anyone of the claims 1 to 4 under conditions suitable for deacylation to occur.

11. A method for producing a semi-synthetic 6-acylated penicillanic acid, a 7-acylated (desacetoxy)cephalosporanic acid or a salt or ester thereof which comprises contacting a corresponding 6-amino or 7-amino β-lactam or salt or ester thereof, respectively, and an acylating agents with a mutant acylase as defined in anyone of the claims 1 to 4 under conditions suitable for acylation to occur.

12. An isolated mutant prokaryotic Penicillin G acylase or its preenzyme or preproenzyme having an amino acid substitution at a position corresponding to A143 (Met) as set forth in SEQ ID NO:27 wherein A143 (Met) is changed to Arg, Lys, Cys, Gly, Thr, or Asp.

* * * * *

UNITED STATES PATENT AND TRADEMARK OFFICE
CERTIFICATE OF CORRECTION

PATENT NO.  : 5,891,703
DATED       : April 6, 1999
INVENTOR(S) : Van Der Laan et al.

It is certified that error appears in the above-identified patent and that said Letters Patent is hereby corrected as shown below:

Title page,
Item [73], delete "Gist-Hrocades", and insert -- Gist-Brocades B.V. --

Column 1,
Line 19, delete "6-amino", and insert -- 6-amino group --
Line 50, delete "Philos,", and insert -- Philos. --

Column 2,
Line 16, delete "Beside", and insert -- Besides --
Line 16, delete "other", and insert -- others --

Column 3,
Line 18, delete "expressed"
Line 27, delete "require", and insert -- requires --
Line 44, delete "adaptation", and insert -- adaptations --

Column 4,
Line 9, delete "less", and insert -- fewer --
Line 28, delete "6-aminopenicillate", and insert -- 6-aminopenicillanate --

Column 5,
Line 62, delete "6-aminopenicillic", and insert -- 6-aminopenicillanic --

Column 6,
Line 39, delete "Km", and insert -- $K_m$ --
Line 42, delete "V$_3$", and insert -- $v_3$ --
Line 45, delete "V$_{-1}$/ V$_3$", and insert -- $v_{-1}/ v_3$ --
Line 56, delete "to amount", and insert -- to the amount --
Line 66, delete "increased", and insert -- decreased --
Line 66, delete "V$_1$/ V$_2$", and insert -- $v_1/ v_2$ --

Column 8,
Line 15, delete "Microbiology 5", and insert -- Microbiology 55 --
Line 41, delete "k$_{cat}$/ Km", and insert -- $k_{cat}/ K_m$ --
Line 67, insert -- penicillin acylase -- between "*E. coli*" and "for"

UNITED STATES PATENT AND TRADEMARK OFFICE
CERTIFICATE OF CORRECTION

PATENT NO. : 5,891,703
DATED : April 6, 1999
INVENTOR(S) : Van Der Laan et al.

Page 2 of 5

It is certified that error appears in the above-identified patent and that said Letters Patent is hereby corrected as shown below:

Column 9,
Line 10, insert -- (vide supra) -- between "et al." and "replaced"
Line 21, delete "position", and insert -- site --

Column 10,
Line 43, delete "FIG. 7", and insert FIG. 6 --
Line 49, delete "FIG. 6", and insert -- FIG. 7 --

Column 11,
Line 33, delete "Pseudomonas sp.", and insert -- *Pseudomonas sp.* --
Line 58, delete "$k_{cat}$/ Km", and insert -- $k_{cat}/K_m$ --

Column 12,
Line 20, delete "steroselectivity", and insert -- stereoselectivity --
Line 30, delete "hydrolases", and insert -- hydrolase --
Line 40, insert -- an -- between "have" and "altered"

Column 13,
Line 2, delete "proteases", and insert -- acylases --
Line 4, delete "sequence", and insert -- sequences --
Line 15, delete "acylase", and insert -- acylases --
Line 36, delete "substrate", and insert -- substrates --
Line 49, delete "to", and insert -- too --
Line 49, delete "methods", and insert -- method --

Column 16,
Line 3, effecting", and insert -- affecting --
Line 27, delete "substituent", and insert -- substituents --
Line 40, delete "Beside", and insert -- Besides --
Line 62, delete "position", and insert -- positions --
Line 65, delete "Position", and insert -- Site --

Column 17,
Lines 9, 10 and 13, delete "oligo's", and insert -- oligos --

UNITED STATES PATENT AND TRADEMARK OFFICE
CERTIFICATE OF CORRECTION

PATENT NO.  : 5,891,703
DATED       : April 6, 1999
INVENTOR(S) : Van Der Laan et al.

It is certified that error appears in the above-identified patent and that said Letters Patent is hereby corrected as shown below:

Column 19,
Line 9, delete "hydrolysis", and insert -- hydrolysis. --
Line 28, delete "wit", and insert -- with --
Line 41, delete "concentration", and insert -- concentrations --

Column 20,
Line 5, delete "quantitated", and insert -- quantified --
Line 41, delete "hydrofobic", and insert -- hydrophobic --

Column 21,
Line 24, delete "B:Asn241", and insert -- B:Asn241. --
Line 41, delete "moiety", and insert -- moiety. --
Line 47, delete "b:Met262", and insert -- B:Met262 --
Line 55, delete "with", and insert -- within --
Line 57, delete "nuber", and insert -- number --

Column 22,
Line 6, delete "with", and insert -- within --
Line 8, delete "nuber", and insert -- number --
Line 37, delete "B175:N", and insert -- B178:N --
Line 43, delete "B65:C", and insert -- B68:C --

Column 23,
Line 13, delete "B455.CG", and insert -- B455:CG --
Line 14, delete "B59:CB", and insert -- B69:CB --
Line 21, delete "B379:CD1", and insert -- B379:OD1 --
Line 23, delete "B360:C", and insert -- B380:C --
Line 40, delete "A147:C1", and insert -- A147:CE2 --
Line 45, delete "B241:CD1", and insert -- B241:OD1 --
Line 50, delete "C8", and insert -- O8 --
Line 59, delete "B384:NO2", and insrt -- B384:ND2 --

Column 24,
Line 13, delete "B241:CD1", and insert -- B241:OD1 --

UNITED STATES PATENT AND TRADEMARK OFFICE
CERTIFICATE OF CORRECTION

PATENT NO. : 5,891,703
DATED : April 6, 1999
INVENTOR(S) : Van Der Laan et al.

It is certified that error appears in the above-identified patent and that said Letters Patent is hereby corrected as shown below:

Columns 25-26,
Line 56, delete "5' GGGR/SCACTGCTGGGCCTCAAG 3' [SEQ ID NO:21]", and insert -- 5' GGGVCACTGCTGGGCCTCAAG 3' [SEQ ID NO:21] --
Line 57, delete "5' AGTGSIYCCCCCAGGCAATCTC 3' [SEQ ID NO:22]", and insert -- 5' AGTGBCCCCCAGGCAATCTC 3' [SEQ ID NO:22] --

Column 25,
Table 5 heading, delete "specifity", and insert -- specificity --
Table 5 heading, delete "reduce", and insert -- reduced --

Column 27,
Table 6 heading, delete "reduce", and insert reduced --

Column 27-28,
Table 7 heading, delete "Catalytic parameters $K_s$ and $v_{sax}$" and insert -- Catalytic parameters $K_m$ and $v_{max}$ --
Table 7, 'wild type' column, delete "$v_{sax}$", and insert -- $v_{max}$ --
Table 7, 'wild type' column, delete "$K_s$", and insert -- $K_m$ --
Table 7, 'A:M143V' column, delete "$v_{sax}$", and insert -- $v_{max}$ --
Table 7, 'A:M143V' column, delete "$K_s$", and insert -- $K_m$ --
Table 7, 'B:L56K' column, delete "$v_{sax}$", and insert -- $v_{max}$ --
Table 7, 'B:L56K' column, delete "$K_s$", and insert $K_m$ --
Table 7, 'A:F147Y' column, delete "$v_{sax}$", and insert -- $v_{max}$ --
Table 7, 'A:F147Y' column, delete "$K_s$", and insert $K_m$ --

Column 28,
Line 36, delete "$(v_{sax}/K_s)_{s1}/(v_{sax}/K_s)_{s2}$", and insert -- $(v_{max}/K_m)_{s1}/(v_{max}/K_m)_{s2}$ --

Column 29,
Line 1 of Table 8, delete "Catalytic parameters $K_s$ and $v_{sax}$" and insert -- Catalytic parameters $K_m$ and $v_{max}$ --
Table 8, column 1, delete "$K_s$", and insert -- $K_m$ --
Table 8, column 2, delete "$V_{sax}$", and insert -- $v_{max}$ --
Table 8, column 3, delete "$V_{sax}/K_s$", and insert -- $v_{max}/K_m$ --
Lines 44-45, delete "$(v_{max}/K_m)^{L-}{}_{PGA}$", and insert -- $(v_{max}/K_m)^{L-PGA}$ --
Line 53, delete "phenylglycineanide", and insert -- phenylglycineamide --
Line 56 of Table 10, delete "$(V_{sax}/K_2)^{D-PGA}/(V_{sax}/K_2)^{L-PAG}$", and insert -- $(v_{max}/K_m)^{D-PGA}/(v_{max}/K_m)^{L-PGA}$ --

UNITED STATES PATENT AND TRADEMARK OFFICE
CERTIFICATE OF CORRECTION

PATENT NO.    : 5,891,703
DATED         : April 6, 1999
INVENTOR(S)   : Van Der Laan et al.

It is certified that error appears in the above-identified patent and that said Letters Patent is hereby corrected as shown below:

Column 30,
Line 1, delete "absorbtion", and isnert -- absorption --
Line 26, delete "vere", and insert -- were --

Column 32,
Line 7, delete "Exprimental", and insert -- Experimental --
Line 8, delete "pE", and insert -- pH --

Column 63,
Line 14, delete "preenzmye", and insert -- preenzyme --
Lines 35-49, replace claim 4 with the following:
4.  A mutant acylase according to claim 3, wherein the amino acid substitution is one of the following:
    B24(Phe) as set forth in SEQ ID NO: 32 to Arg or Lys;
    B56 (Leu) as set forth in SEQ ID NO: 32 to Arg, Lys, His, Gly, Ala or Val;
    B177 (Ile) as set forth in SEQ ID NO: 32 to Arg, Lys, His, Val, Met, or Ser or Thr;
    B71 (Pro) as set forth in SEQ ID NO: 32 to Phe or Tyr; or
    B67 (Ala), B68 (Thr) or B69 (Ala) as set forth in SEQ ID NO: 32 to any other amino acid.

Signed and Sealed this

Eleventh Day of December, 2001

*Attest:*

*Attesting Officer*

NICHOLAS P. GODICI
*Acting Director of the United States Patent and Trademark Office*